US011733192B2

(12) United States Patent
Swager et al.

(10) Patent No.: US 11,733,192 B2
(45) Date of Patent: Aug. 22, 2023

(54) SWITCHABLE SINGLE-WALLED CARBON NANOTUBE-POLYMER COMPOSITES FOR $CO_2$ SENSING

(71) Applicant: MASSACHUSETTS INSTITUTE OF TECHNOLOGY, Cambridge, MA (US)

(72) Inventors: Timothy Swager, Newton, MA (US); Bora Yoon, Cambridge, MA (US); Gary Walsh, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 762 days.

(21) Appl. No.: 16/574,012

(22) Filed: Sep. 17, 2019

(65) Prior Publication Data
US 2020/0088668 A1     Mar. 19, 2020

Related U.S. Application Data

(60) Provisional application No. 62/732,541, filed on Sep. 17, 2018.

(51) Int. Cl.
| | |
|---|---|
| *C08F 226/06* | (2006.01) |
| *G01N 27/12* | (2006.01) |
| *G01N 33/00* | (2006.01) |
| *C08K 3/04* | (2006.01) |

(52) U.S. Cl.
CPC ......... *G01N 27/126* (2013.01); *C08F 226/06* (2013.01); *C08K 3/041* (2017.05); *G01N 27/127* (2013.01); *G01N 33/004* (2013.01); *C08K 2201/001* (2013.01); *C08K 2201/011* (2013.01)

(58) Field of Classification Search
CPC .... C08F 112/22; C08F 112/26; C08F 212/22; C08F 212/26; C08F 226/06; C08L 39/08; C08L 57/12; G01N 27/126; G01N 27/127; G01N 33/004; C08K 2201/001; C08K 2201/011; C08K 3/041
See application file for complete search history.

(56) References Cited

U.S. PATENT DOCUMENTS

| | | | |
|---|---|---|---|
| 5,324,792 A * | 6/1994 | Ford | C08F 8/12 525/379 |
| 8,679,859 B2 | 3/2014 | Yan et al. | |
| 9,085,715 B2 | 7/2015 | Berthelot et al. | |
| 10,106,403 B2 | 10/2018 | Mayne-L'Hermite | |
| 10,697,918 B2 * | 6/2020 | Swager | G01N 27/127 |
| 2009/0286308 A1 | 11/2009 | Berthelot et al. | |
| 2010/0028559 A1 | 2/2010 | Yan et al. | |
| 2011/0244585 A1 | 10/2011 | Mayne-L'Hermite et al. | |

OTHER PUBLICATIONS

International Search Report and Written Opinion of the International Searching Authority for PCT/US2019/051598 dated Jan. 23, 2020.
Layek et al. "A review on synthesis and properties of polymer functionalized graphene" Polymer. Jun. 26, 2013 (Jun. 28, 2013) vol. 54, p. 5087-5103; p. 5091, Fig. 4.
Invitation to Pay Additional Fees for PCT/US2019/051598 dated Nov. 18, 2019.

* cited by examiner

*Primary Examiner* — Mark Kopec
*Assistant Examiner* — Jaison P Thomas
(74) *Attorney, Agent, or Firm* — Honigman LLP

(57) ABSTRACT

A sensor for carbon dioxide can include an amidine functional group.

17 Claims, 27 Drawing Sheets

SWITCHABLE SINGLE-WALLED CARBON NANOTUBE-POLYMER COMPOSITES FOR $CO_2$ SENSING

PRIORITY CLAIM

The application claims priority from U.S. Provisional Patent Application No. 62/732,541, filed Sep. 17, 2018, which is incorporated by reference in its entirety.

GOVERNMENT SPONSORSHIP STATEMENT

This invention was made with Government support under Grant No. W911NF-13-D-0001 awarded by the Army Research Office (ARO). The Government has certain rights in the invention.

TECHNICAL FIELD

The invention features a composition and sensor for detecting carbon dioxide.

BACKGROUND

There has been a growing interest in the detection and monitoring $CO_2$ in agri-food industry for precise agriculture and high food quality packaging. Determination of optimal $CO_2$ levels in greenhouse crop production, which controls the photosynthesis of plants, is important to improve crop productivity. Increasing the $CO_2$ level to 0.1% increases photosynthesis of most crops by about 50% over atmospheric $CO_2$ levels while an excessive amount of $CO_2$ may cause damage to plants. In the food packaging, $CO_2$ generated by the microbial metabolic activity is a key food spoilage indicator. Monitoring of $CO_2$ levels in foods packed with modified atmosphere packaging (MAP) is also required to ensure food quality and predict shelf life. In MAP, a $CO_2$ level of 20-80% is required in the package headspace for non-respiring food to decrease the growth rate of aerobic bacteria. Elevated $CO_2$ (>1%) and reduced $O2$ (<8%) levels can retard fruit ripening by inhibiting ethylene production, thereby increasing shelf life. When monitoring $CO_2$ in a food package, the optimal relative humidity (RH) depends on the type of produce: dried products (<70%) or fresh-cut produce (>95%).

SUMMARY

In one aspect, a composition can include a polymer including amino side chain and an alkylazide side chain, and a conductive material associated with the polymer.

In another aspect, a composition can include an amidine-functional polymer associated with a carbon conductive material. In certain circumstances, the amidine-functional polymer can be derived from an alkylazido group of a polymer.

In another aspect, a sensor for detecting carbon dioxide can include a substrate and an amidine-functional polymer associated with a carbon conductive material on the substrate. In some embodiments, the amidine-functional polymer can be immobilized on a surface of the substrate.

In another aspect, a method of detecting carbon dioxide can include exposing a composition including an amidine-functional polymer associated with a carbon conductive material to a sample, and measuring the conductivity change of the composition.

In another aspect, a method of preparing a sensor for detecting an analyte can include associating a polymer including amino side chain and an alkylazide side chain with a conductive material, linking the polymer associated with the conductive material to a substrate, quaternizing the amino side chain, and functionalizing the alkylazide side chain. In some embodiments, functionalizing the alkylazide side chain can include introducing a amidine-functional group to the side chain.

In certain circumstances, the conductive material can include a carbon nanotube, a conductive polymer, an inorganic semiconductor, a metal oxide, a carbon fiber, a carbon particle, graphite, graphene, carbon paste, metal particles, or conducting ink, or combination thereof. For example, the conductive material can be a carbon conductive material, such as graphene or a carbon nanotube. In certain circumstances, the conductive material or carbon conductive material can be a single-walled carbon nanotube.

In certain circumstances, the polymer can be a random copolymer. For example, the polymer can be a copolymer of an amine-containing monomer and an alkylazide monomer.

In certain circumstances, the amine-containing monomer can be a vinyl pyridine. In some embodiments, the pyridine group can quaternized.

In certain circumstances, the alkylazide monomer can be an alkylazido vinyl benzene, for example, an azidoethoxy vinyl benzene. In some embodiments, the azidoethoxy group can be an ethylene oxide oligomer, for example, azidoethoxyethoxy or azidoethoxyethoxyethoxy.

In certain circumstances, the polymer can be a copolymer of vinyl pyridine and alkylazido vinyl benzene.

In certain circumstances, the amidine-functional polymer can be a random copolymer.

In certain circumstances, the amidine-functional polymer can be a copolymer of an amine-containing monomer and an amidine-functional monomer.

Other aspects, embodiments, and features will be apparent from the following description, the drawings, and the claims.

BRIEF DESCRIPTION OF THE DRAWINGS

FIG. 2A shows a schematic of surface functionalization of a chemiresistive $CO_2$ sensor. FIG. 2B shows a UV-vis-NIR absorption spectrum of the diluted P(4VP-VBAz)-SWCNT dispersion (1:3 dilution in DMF). Inset: photograph of the undiluted P(4VP-VBAz)-SWCNT dispersion in DMF. FIG. 2C shows ATR-FTIR spectra of the P(4VP-VBAz)-SWCNT, P(Q4VP-VBAz)-SWCNT and P(Q4VP-VBAm)-SWCNT composite films on glass substrates. FIG. 2D shows Raman spectra of P(4VP-VBAz)-SWCNT and P(Q4VP-VBAm)-SWCNT films normalized to the G band at 1589 cm$^{-1}$ (excitation at 633 nm).

FIG. 4A shoes chemiresistive responses averaged over four devices of P(4VP-VBAz)-SWCNT, P(Q4VP-VBAz)-SWCNT and P(Q4VP-VBAm)-SWCNT in response to 200 s exposure to 2% $CO_2$ in $N_2$ (RH 53%). Inset: average conductance trace of four P(Q4VP-VBAm)-SWCNT devices in response to 200 s exposure to 2% $CO_2$ in $N_2$ (RH 53%). FIG. 4B shows average conductance traces of four devices of P(Q4VP-VBAm)-SWCNT in response to repeated 200 s exposure to 2% $CO_2$ in $N_2$ (RH 53%). FIG. 4C shows average conductance response of four P(Q4VP-VBAm)-SWCNT devices in response to 200 s exposure of varying concentrations of $CO_2$ in $N_2$ (RH 53%). FIG. 4D shows chemiresistive responses averaged over four P(Q4VP-VBAm)-SWCNT devices in response to 200 s exposure to 2% $CO_2$ in $N_2$ under various relative humidity conditions at 21° C. and FIG. 4E shows their chemiresistive traces. The shaded areas indicate the standard deviations (N=4 sensors).

FIGS. 5A and 5B depict a comparison of device performance between devices fabricated with Cu-containing P(4VP-VBAz)-SWCNT and P(Q4VP-VBAz)-SWCNT versus P(Q4VP-VBAm)-SWCNT in response to 200 s exposure to 2% $CO_2$ in $N_2$ (RH 53%). FIG. 5A shows average conductance traces of four devices of (i) Cu-containing P(4VP-VBAz)-SWCNT, (ii) Cu-containing P(Q4VP-VBAz)-SWCNT and P(Q4VP-VBAm)-SWCNT and FIG. 5B shows their average normalized conductance responses. FIG. 5C shows average conductance traces of four devices of P(Q4VP-VBAm)-SWCNT in response to 200 s exposure to 20% 02 (green) and 1% Ar (yellow) in $N_2$, respectively (RH 53%). FIG. 5D shows chemiresistive responses averaged over four P(Q4VP-VBAm)-SWCNT devices in response to 200 s exposure to 20% 02 and 1% Ar in $N_2$, respectively, and 200 s exposure to 2% $CO_2$ in air (RH 53%). The shaded areas indicate the standard deviations (N=4 sensors).

FIG. 16A shows a 41 NMR spectrum of PDAA in dry DMSO-$d_6$. FIG. 16B shows a 41 NMR spectrum of PDAA in wet DMSO-$d_6$ recorded after bubbling $CO_2$ through the solution for 2 min. FIG. 16C shows a 41 NMR spectrum subsequent to Ar bubbling through the same solution for 2 min.

FIG. 22A shows ATR-FTIR spectra of P(4VP-VBAz)-SWCNT and P(Q4VP-VBAz)-SWCNT composite films on glass substrates before and after Cu incorporation. FIG. 22B shows an XPS wide scan of Cu—P(4VP-VBAz)-SWCNT and FIG. 22C shows its high resolution N is spectrum. FIG. 22D shows an XPS wide scan of Cu—P(Q4VP-VBAz)-SWCNT (* shows a trace of F impurity) and FIG. 22E shows its high resolution N 1 s spectrum.

DETAILED DESCRIPTION

Figure 1:
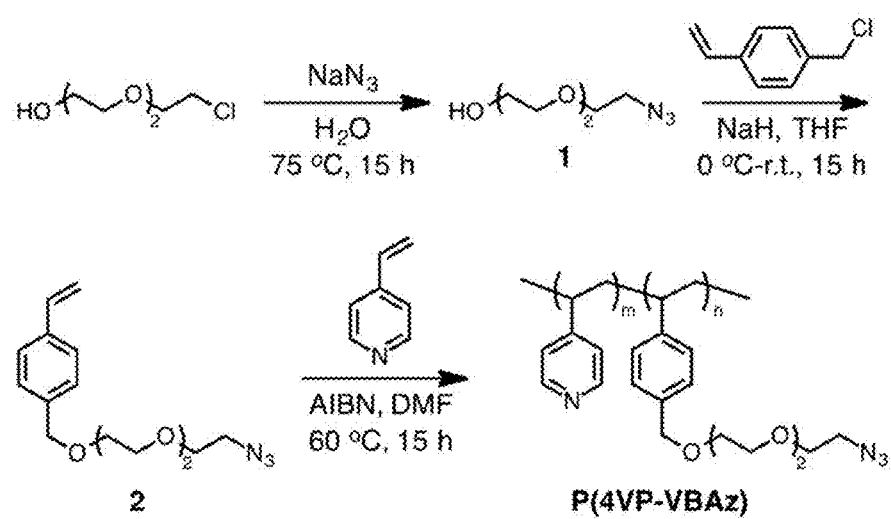
FIG. 1 is a schematic showing synthesis of P(4VP-VBAz) copolymer.

A chemiresistive $CO_2$ sensor based on single-walled carbon nanotubes (SWCNTs) noncovalently functionalized with a $CO_2$ switchable copolymer containing amidine pendant groups that transform into amidinium bicarbonates in response to $CO_2$ is described. To fabricate a robust surface-anchored polymer-SWCNT dispersion via spray-coating, a precursor copolymer, P(4VP-VBAz), bearing both 4-vinylpyridine (4VP) groups and azide groups was designed and synthesized. The SWCNT dispersant group, 4VP, is capable of debundling and stabilizing nanotubes to improve their solubility in organic solvents for solution processing. Well-dispersed P(4VP-VBAz)-SWCNT composites are covalently immobilized onto a glass substrate functionalized with alkyl bromides, then the amidine moieties are subsequently attached to form resulting $CO_2$-switchable P(Q4VP-VBAm)-SWCNT composites via copper(I)-catalyzed azide-alkyne cycloaddition click reaction at the film surface. The amidine groups are strong donors that compensate or pin carriers in the SWCNTs. In the presence of $CO_2$ under humid conditions, the generated amidinium bicarbonates from the polymer wrapping increase the concentration and/or liberate hole carriers in the nanotubes, and thereby increasing the net conductance of the composites. The amidinium moieties revert back to the amidines when purged with a $CO_2$ free carrier gas with a reversible decrease in conductance. High selectivity to $CO_2$ over the other atmospheric gases such as $O_2$ and Ar is observed.

A composition can include a polymer including amino side chain and an alkylazide side chain, and a conductive material associated with the polymer. In certain circumstances, the amidine-functional polymer can be derived from an alkylazido side chain or group of a polymer. The conductive material can be a carbon conductive material. The association of the polymer with the conductive material allows the conductivity of the composition to change when exposed to an analyte. For example, when the composition includes an amidine-functional polymer associated with a carbon conductive material, the amidine-functional polymer interacts with carbon dioxide or carbonic acid, or a carbonate to alter the electronic environment near the conductive material, leading to a change in conductivity. This can lead to development of a sensor for detecting carbon dioxide, which can include a substrate and an amidine-functional polymer associated with a carbon conductive material on the substrate. In some embodiments, the amidine-functional polymer can be immobilized on a surface of the substrate. The sensor can identify the presence of carbon dioxide by measuring the conductivity change of the composition. The sensor can be reversible, meaning that when purged with a gas that does not include carbon dioxide, the conductivity of the composition returns to a less conductive state.

In certain circumstances, the conductive material can include a carbon nanotube, a conductive polymer, an inorganic semiconductor, a metal oxide, a carbon fiber, a carbon particle, graphite, graphene, carbon paste, metal particles, or conducting ink, or combination thereof. For example, the conductive material can be a carbon conductive material, such as graphene or a carbon nanotube. In certain circumstances, the conductive material or carbon conductive material can be a single-walled carbon nanotube.

The polymer can be a random copolymer. For example, the polymer can be a copolymer of an amine-containing monomer and an alkylazide monomer. The polymer can be a polystyrene. The amine-containing monomer can be a vinyl pyridine. In some embodiments, the pyridine group or the amino group can quaternized, for example, by exposing the pyridine group or the amino group to an alkylhalide or other alkylating agent.

The alkylazide monomer can be an alkylazido vinyl benzene, for example, an azidoethoxy vinyl benzene or an azidoethyl vinyl benzene. In some embodiments, the azidoethoxy group can be an ethylene oxide oligomer, for example, azidoethoxyethoxy or azidoethoxyethoxyethoxy. In other embodiments, the azidoethyl group can be an ethylene oligomer, for example, azidobutyl or azidohexyl.

The azido group can be transformed, for example, using click chemistry, to add another functional group to the composition that can interact or react with the analyte. For example, a functional alkyne undergo a click cyclization to form a triazo-ring moiety. The functionalization can introduce the amindine functionality to the polymer.

A building block approach to the polymer can allow the sensor to be built in sequential fashion. First, a polymer including amino side chain and an alkylazide side chain can be associated with a conductive material. For example, a polyvinylpyridine copolymer can be associated with a carbon nanotube. The associated polyvinylpyridine copolymer and nanotube can be immobilized onto a surface of a substrate using a silane linker, for example, bromoethyltricholorosilane.

The polyvinylpyridine copolymer can have residual pyridine groups quaternized, for example, by reaction with an alkylhalide or other alkylating group, such as ethylbromide. The quaternization can be done to other amino groups. By quaternizing, the electronic properties of the underlying carbon material can be accessed and monitored.

The polyvinylpyridine copolymer includes a comonomer with an azido functional group. The azido functional group can undergo click chemistry reactions to introduce another functional group, such as an amidine. The amidine can reversibly react with carbon dioxide in the presence of water, allowing for detection of carbon dioxide with the amidine-based sensor. The resistivity or conductivity of the sensor can change when the sensor is exposed to an analyte. A conductive material conducts electricity. The conductive material can include a carbon nanotube, a conductive polymer, an inorganic semiconductor, or a metal oxide. The conductive material can include a metal, an organic material, a dielectric material, a semiconductor material, a polymeric material, a biological material, a nanowire, a semiconducting nanoparticle, a nanofiber, a carbon fiber, a carbon particle, graphite, graphene, carbon paste, metal particles, or conducting ink, or combination thereof. The conductive material can include an organic electronic material, a conductive polymer, a doped conjugated polymer, or a conductive inorganic material. When the conductive material is a conductive carbon material, the conductive material can be a carbon nanotube such as a single-walled carbon nanotube (SWNT), or graphene.

A conductive polymer can include a poly(fluorene), a polyphenylene, a polypyrene, a polyazulene, a polynaphthalene, a poly(pyrrole) (PPY), a polycarbazole, a polyindole, a polyazepine, a polyaniline (PANI), a poly(thiophene) (PT), a poly(3,4-ethylenedioxythiophene) (PEDOT), a poly(p-phenylene sulfide) (PPS), a poly(acetylene) (PAC), a poly (p-phenylene vinylene) (PPV), or copolymers thereof. A metal oxide can include $ZnO_2$, $SnO_2$, $TiO_4$, $WO_3$, $MoO_3$, NiO, SnO, or combinations thereof. The inorganic semiconductor can include $MoS_2$, $MoSe_2$, $ZnS_2$, Si, Ge, InP, or combinations thereof.

Single-walled carbon nanotubes (SWCNTs) are attractive materials for sensing such gaseous analytes because of their sensitive resistance changes in response to the binding of molecules. Chemical functionalization of SWCNTs with selectors or receptors via covalent/noncovalent functionalization can produce sensors selective to target analytes. Noncovalent functionalization of SWCNTs offers the advantage of minimal perturbation of the electronic properties of the nanotubes, as opposed to covalent functionalization, which disrupts the extended π-electronic states in the nanotube sidewalls. This can be accomplished by using polymer wrappers to debundle SWCNTs through noncovalent interactions to form a stabilized dispersion in solvent media.

A modular chemiresistive sensor platform can be fabricated with SWCNT dispersions stabilized by noncovalently wrapping with poly(4-vinylpyridine) (P4VP). The pyridyl groups of P4VP enable the high stability of the dispersion by debundling nanotubes, but also afford efficient post-functionalization with transition metals or enzymes to create selective sensors. Recognizing the advantages of P4VP as a modular SWCNT dispersant, it was hypothesized that SWCNT composites functionalized with a copolymer containing both the pyridyl group and a $CO_2$-responsive group provides a new chemiresistive sensor platform for $CO_2$ sensing.

Of interest to the present study are amidines, analogues of carboxylic acids and esters containing two nitrogens, as $CO_2$ responsive units. Since its introduction by Jessop and coworkers, amidine has attracted great attention as a $CO_2$-switchable group due to its high basicity, and facile capture and release of $CO_2$. Specifically, amidines are reversibly transformed into cationic amidinium bicarbonate salts in the presence of $CO_2$ and water. Indeed, polymers containing a pendant amidine group have been widely studied over the past few years for their use in $CO_2$-switchable vesicles, microtubules and latexes, and $CO_2$ capture. Previous studies on SWCNT-amidine have focused on reversible polarity changes in a mixed solvent system.

Herein, a chemiresistive $CO_2$ sensor fabricated with SWCNT composites functionalized with a $CO_2$-switchable copolymer is described. To create a robust surface-anchored polymer-SWCNT dispersion via spray-coating, the previous approach can be extended wherein pyridyl groups from the P4VP-SWCNT composites are covalently immobilized onto a glass substrate functionalized with alkyl bromides. A wrapper polymer, P(4VP-VBAz), bearing both 4VP groups and azide groups (FIG. 1), can form a stable composite with SWCNTs. This azide-tethered precursor polymer allows the immobilizing quaternization of 4VP groups of the polymer-SWCNT. The residual pyridyl groups can be functionalized, not consumed in this quaternization, by reaction with bromoethane to inhibit the Lewis basic pyridyl nitrogens from electron donation to the graphene sidewalls or scattering/pinning carriers, which limit the transport through the SWCNTs. Once immobilized and alkylated, the amidine moieties can be introduced via "click" reaction to produce $CO_2$-switchable P(Q4VP-VBAm)-SWCNT composites (FIG. 2A). The sensor shows a reversible chemiresistive response in the presence of gaseous $CO_2$ under humid conditions and selectivity to $CO_2$ over the other atmospheric gases such as $O_2$ and Ar.

Figure 2A:
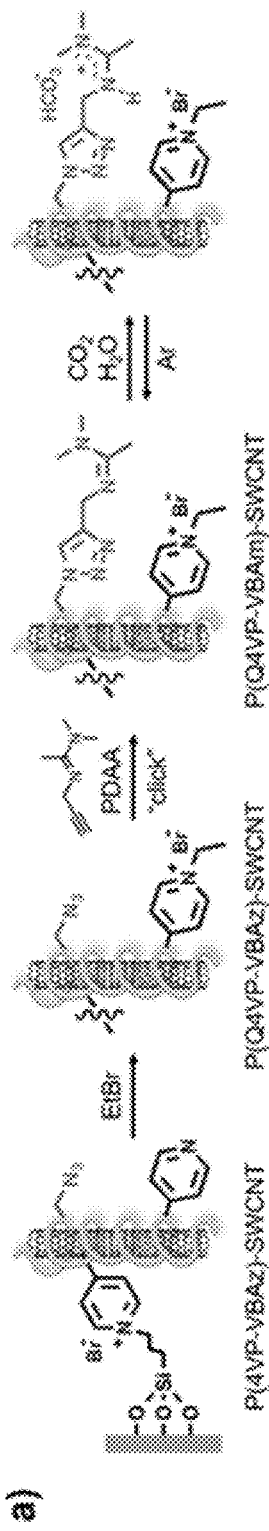
FIGS. 2A-2D depict properties of a sensor.
Figure 12A:
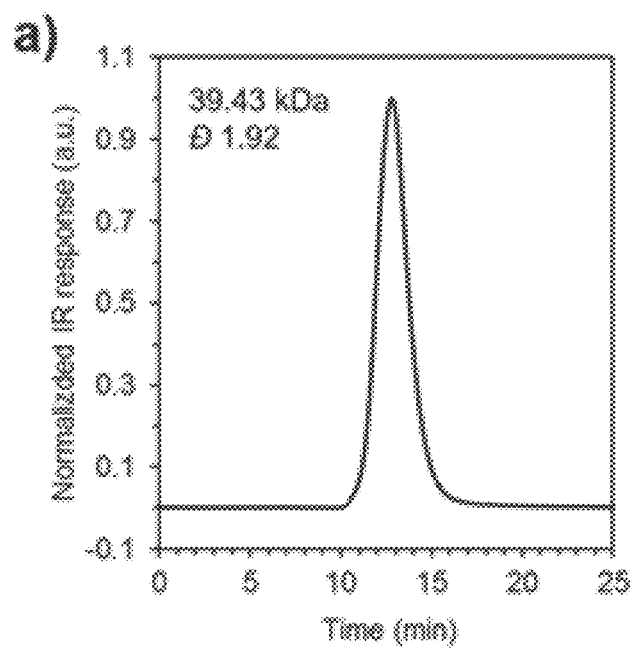
FIGS. 12A-12B depict a GPC trace (DMF with 0.025 M LiBr as eluent at 60° C.) and $^1$H NMR spectrum of P(4VP-VBAz) in DMSO-$d_6$, respectively.
Figure 12B:
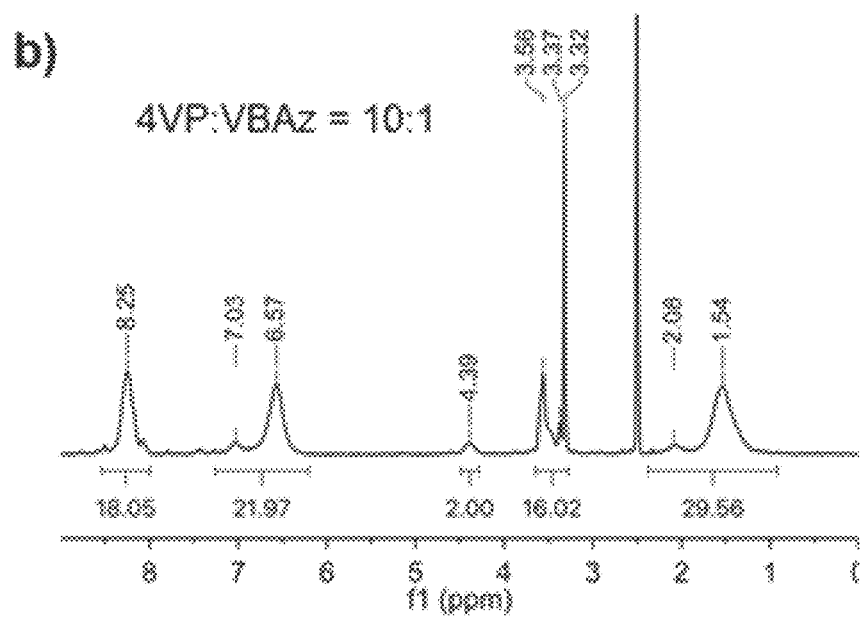

The polymer wrapper P(4VP-VBAz) bearing pyridyl and azide groups was synthesized via free radical polymerization (FIG. 1). Monomer 2 was prepared by a substitution reaction of di(ethylene oxide)-tethered azide 1 with 4-vinylbenzyl chloride. The polymerization of 2 and 4-vinylpyridine was conducted in dry DMF at 60° C. using AIBN as a thermal initiator under inert atmosphere. The gel permeation chromatography in DMF provided a $M_n$ of 39.43 kDa (Đ=1.92). The ratio of 4VP to 2 was found to be 10:1 based on NMR integration (FIGS. 12A-12B).

Figure 2B:
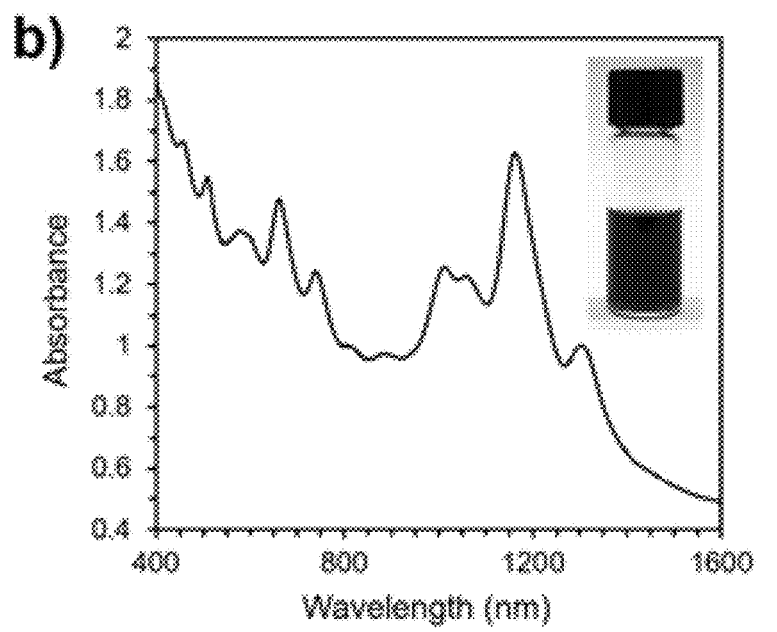
Figure 13:
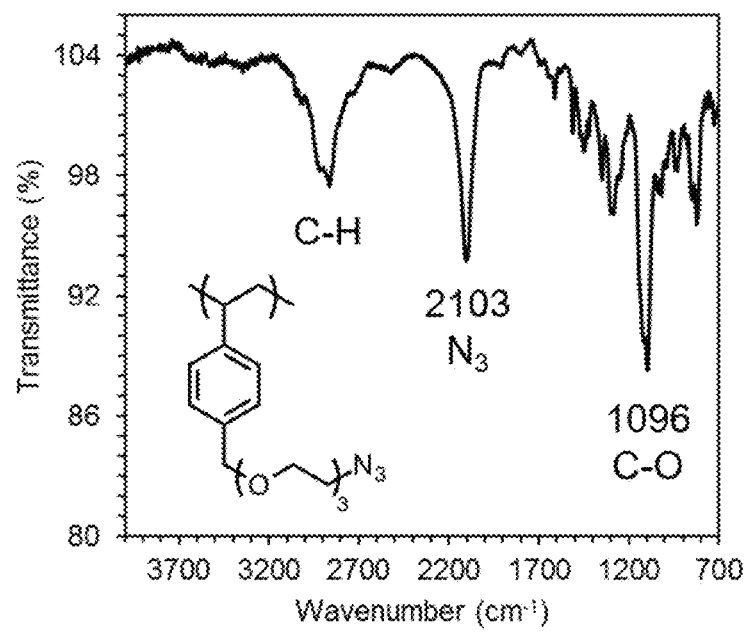
FIG. 13 is an ATR-FTIR spectrum of P(VBAz).

A dispersion of P(4VP-VBAz)-SWCNT was prepared as follows. Briefly, a mixture of CoMoCAT SWCNTs with an average diameter of 0.82 nm (5 mg) and polymers (50 mg) in 10 mL of DMF was sonicated for 1 h in an ultrasonic ice bath and then centrifuged for 30 min at 15,000 g to remove non-dispersed particulate materials. The undiluted supernatant, shown in FIG. 2B (inset), P(4VP-VBAz) is highly stable and concentrated SWCNT dispersion with no observable precipitation. The dispersion was found to be stable for at least 3 months under benchtop conditions. A UV-vis-NIR spectrum of the diluted P(4VP-VBAz)-SWCNT dispersion (1:3 dilution in DMF) shows absorption bands from 800 nm to 1600 nm and from 550 to 900 nm, indicative of the $E_{11}$ and $E_{22}$ van Hove singularity transitions of semiconducting SWCNTs, respectively (FIG. 2B). The transitions of the metallic tubes are also present in the region from 400 to 600 nm, suggesting that both semiconducting and metallic nanotubes are present in the dispersion. The well-resolved absorptions are indicative of individual (debundled) nanotubes. For comparative purposes we attempted to synthesize a homopolymer of 2 (FIG. 13). However, only DMF insoluble gels were produced and hence we have focused on synthesized copolymer.

To create a surface-immobilized precursor sensor platform, 0.3 mL of the P(4VP-VBAz)-SWCNT dispersion was spray-coated on a glass substrate functionalized with 3-bromopropyltrichlorosilane following a previously described procedure (FIG. 2A). It should be noted that if the amidine were present in the polymer at this first immobilization step, the amidine's high basicity (conjugate acid pKa≈12) can produce side reactions. Therefore the azide-tethered precursor polymer ensures that the covalent anchoring occurs between the pyridyl groups and the surface alkyl bromides. In a subsequent step, the residual pyridyl groups are quaternized by reaction with bromoethane. The Lewis basic nature of the pyridyl groups impedes hole transport in the SWCNTs and alkylation liberates carriers that were trapped by the interactions with the nitrogen lone pairs. In a last step, amidine moieties can be introduced via a "click" reaction to form $CO_2$-switchable P(Q4VP-VBAm)-SWCNT composites.

Figure 2C:
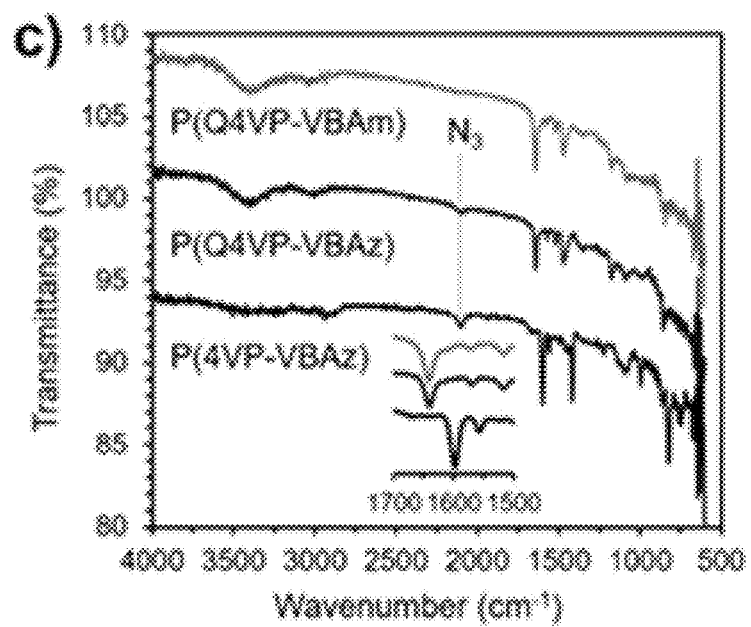

The surface reactions used in preparing the SWCNT composite films were confirmed by FTIR spectroscopy (FIG. 2C). P(4VP-VBAz)-SWCNT displays characteristic bands at 2103 and 1598 $cm^{-1}$ attributed to the azide and pyridyl C=N groups, respectively. Quaternization by reaction with bromoethane results in a shift of the C=N band to 1642 $cm^{-1}$ to give the quaternized material P(Q4VP-VBAz)-SWCNT. The disappearance of —$N_3$ band at 2103 $cm^{-1}$ confirms the formation of P(Q4VP-VBAm)-SWCNT by click reaction.

Figure 2D:
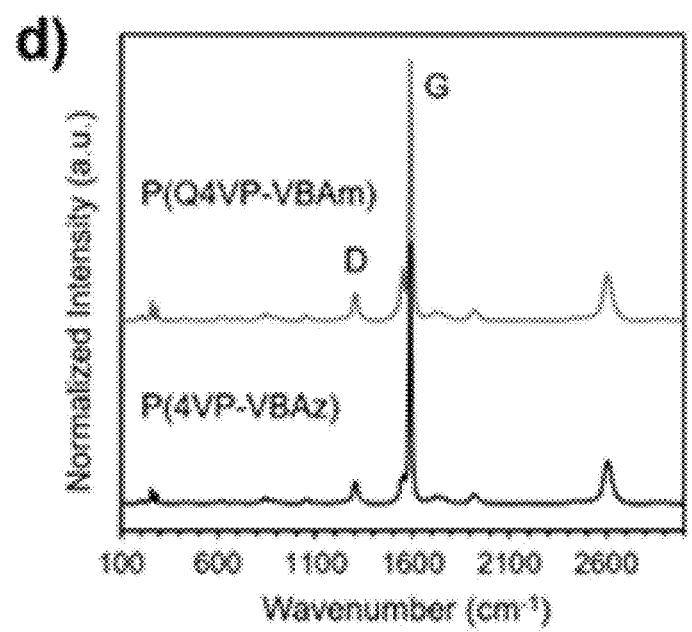
Figure 14:
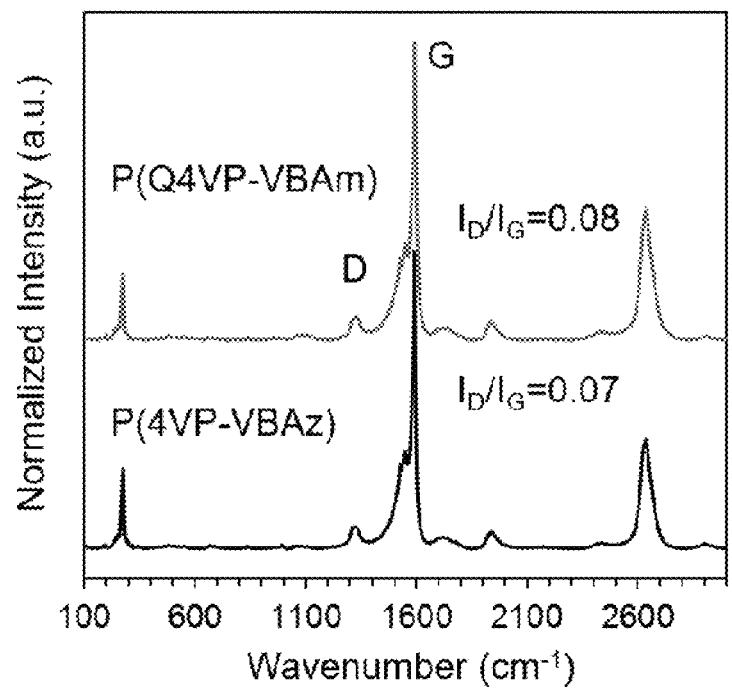
FIG. 14 depicts Raman spectra of P(4VP-VBAz)-SWCNT and P(Q4VP-VBAm)-SWCNT films normalized to G band at 1590 and 1591 cm$^{-1}$, respectively (excitation at 532 nm).

The SWCNTs are noncovalently wrapped with the polymer, and as a result the two-step functionalization on the polymer does not cause severe disruption of then-electronic states in the nanotube sidewalls, which is confirmed by Raman spectroscopy (633 nm excitation, FIG. 2D). The intensity ratio of D to G band is indicative of the defects in the SWCNT sidewalls, and only increased slightly from 0.08 in P(4VP-VBAz)-SWCNT to 0.10 in P(Q4VP-VBAm)-SWCNT, with functionalization. Raman spectra recorded using an excitation wavelength of 532 nm shows a similarly modest D/G increase from 0.07 to 0.08, suggesting that the current surface functionalization strategy preserves the electrical transport properties of SWCNTs (FIG. 14).

Figure 3A:
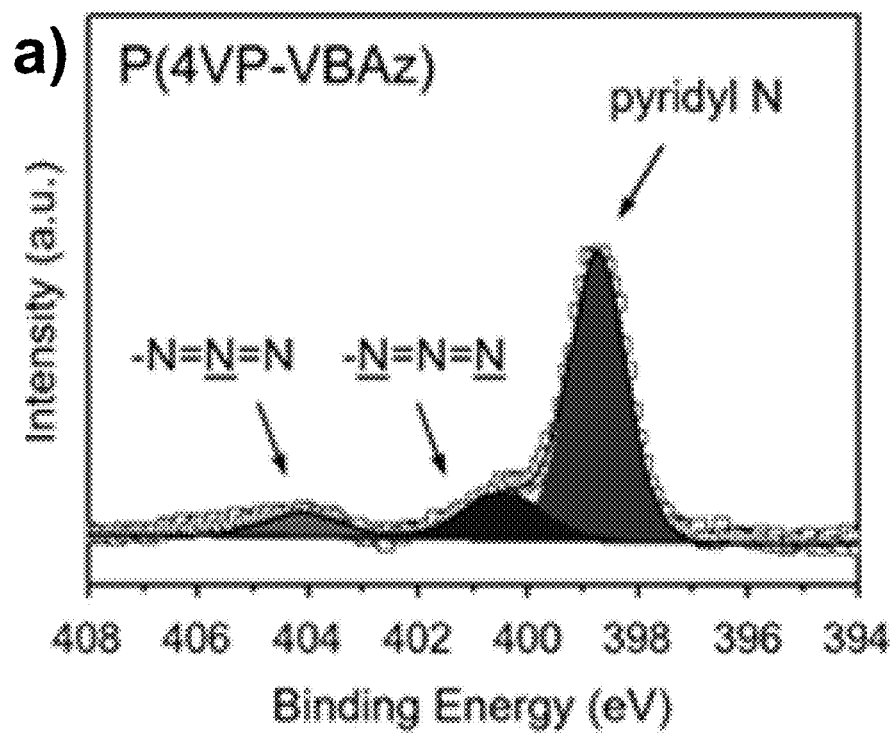
FIGS. 3A-3C show high resolution XPS spectra of N is of (a) P(4VP-VBAz)-SWCNT in FIG. 3A, P(Q4VP-VBAz)-SWCNT in FIG. 3B and P(Q4VP-VBAm)-SWCNT films in FIG. 3C on glass substrates.
Figure 3B:
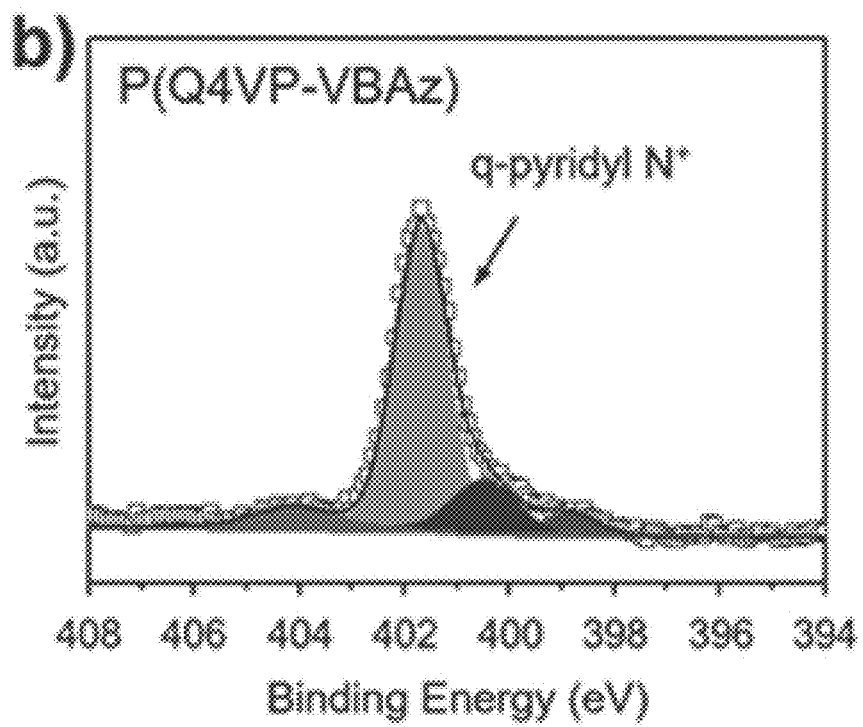
Figure 3C:
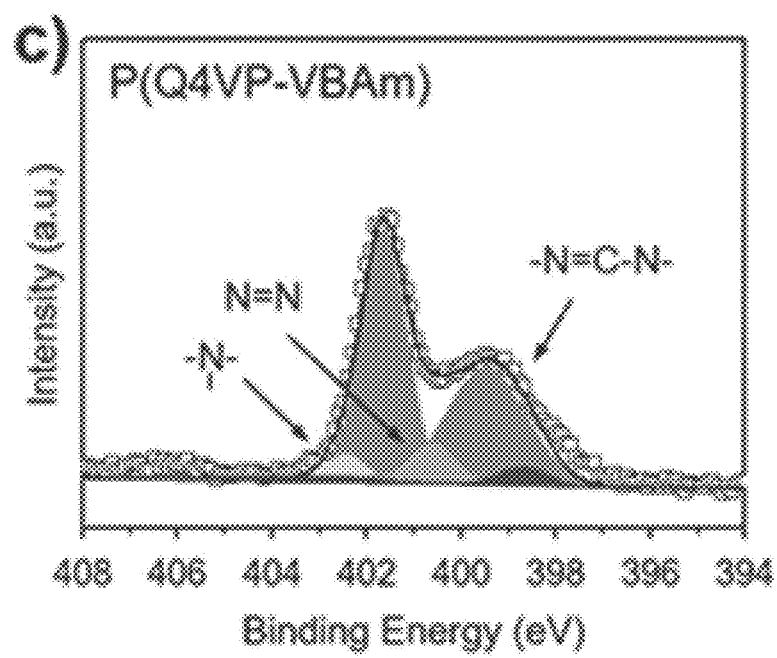
Figure 15A:
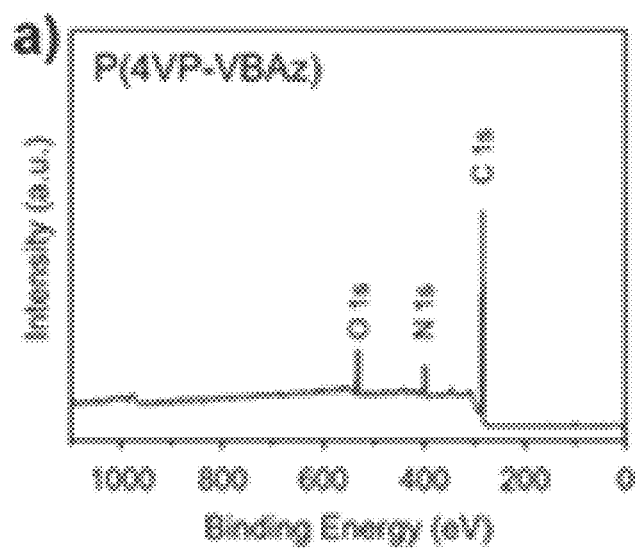
FIGS. 15A-15C depict XPS wide scans of (FIG. 15A) P(4VP-VBAz)-SWCNT, (FIG. 15B) P(Q4VP-VBAz)-SWCNT and (FIG. 15C) P(Q4VP-VBAm)-SWCNT films on glass substrates.
Figure 15B:
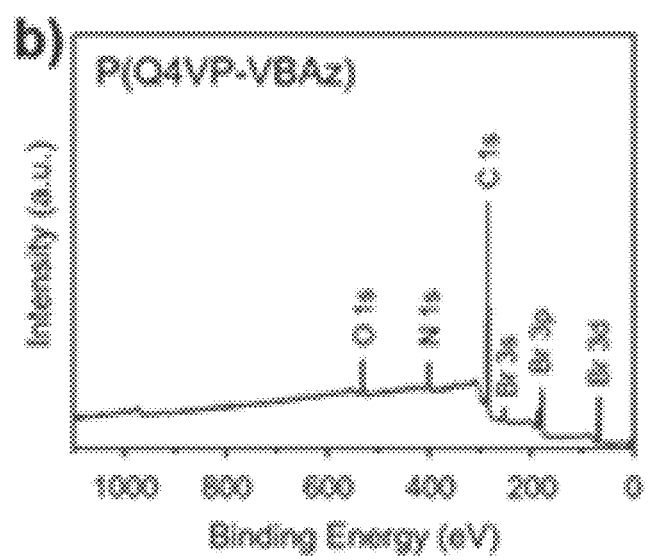
Figure 15C:
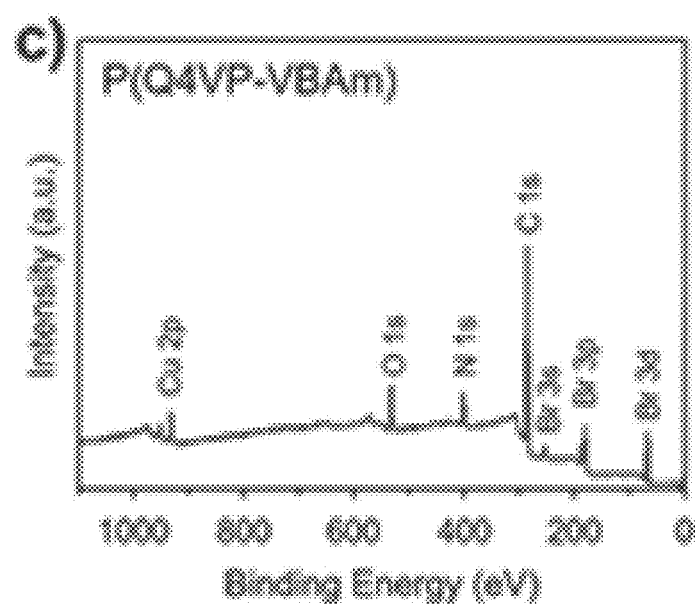

The progression of the active film formation was further confirmed by X-ray photoelectron spectroscopy (XPS) as shown in FIG. 3. The high resolution N is spectrum of P(4VP-VBAz)-SWCNT has a pyridyl N peak at 398.8 eV and two distinctive peaks corresponding to the azide group at 400.5 and 404.1 eV with a peak area ratio of 1:0.2:0.1, which is consistent with the ratio found from the NMR characterization (FIG. 3A). After the bromoethane treatment, the pyridyl N 1 s peak shifts to a higher binding energy at 401.7 eV, attributed to the quaternized pyridinium nitrogen of P(Q4VP-VBAz)-SWCNT, while the azide peaks remain unchanged (FIG. 3B). A free pyridine peak is still observed from the deconvoluted spectrum of P(Q4VP-VBAz)-SWCNT, however 92% of pyridine is estimated to be quaternized based on the integrated areas centered at 398.8 and 401.7 eV. In FIG. 3C, the subsequent click reaction at the film surface was evidenced by the absence of the azide peak at 404.1 eV in the high resolution N is spectrum of P(Q4VP-VBAm)-SWCNT. In addition, the two deconvoluted peaks at 400.6 and 402.5 eV are attributed to the formation of triazole ring and the newly appeared broad peak centered at 399.5 eV indicates the amidine moieties. A trace residual Cu ion from the XPS wide scan survey of P(Q4VP-VBAm)-SWCNT were observed even after repeated washing with pure acetonitrile and water, which will be discussed below (FIGS. 15A-15C).

Figure 16A:
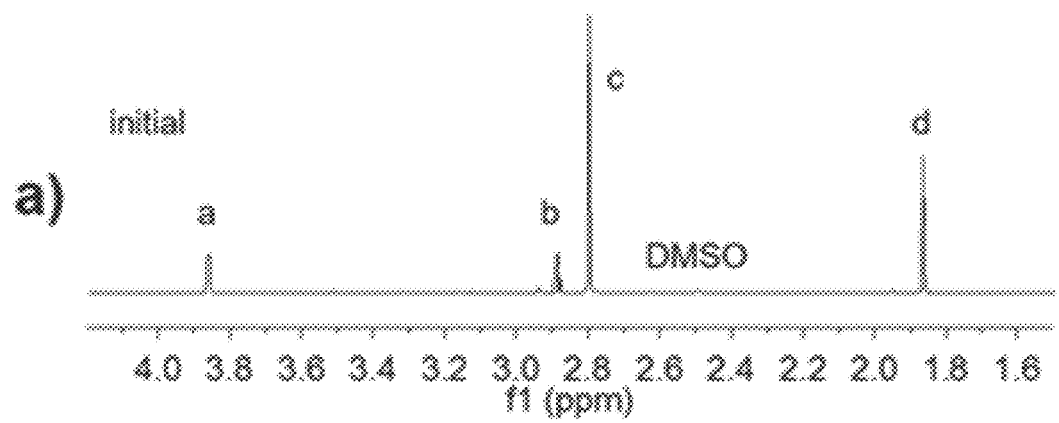
FIGS. 16A-16C depict spectral response of a moiety with carbon dioxide.
Figure 16A:
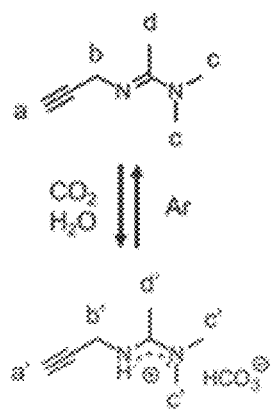
Figure 16B:
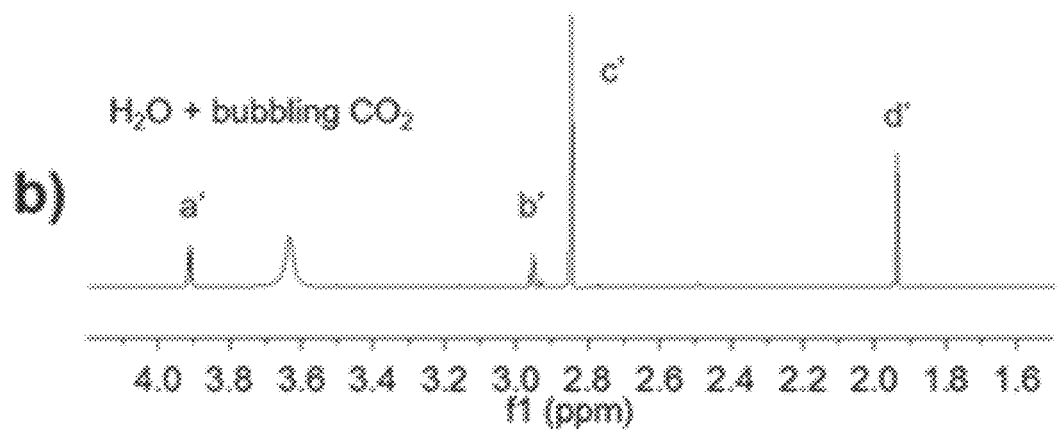
Figure 16C:
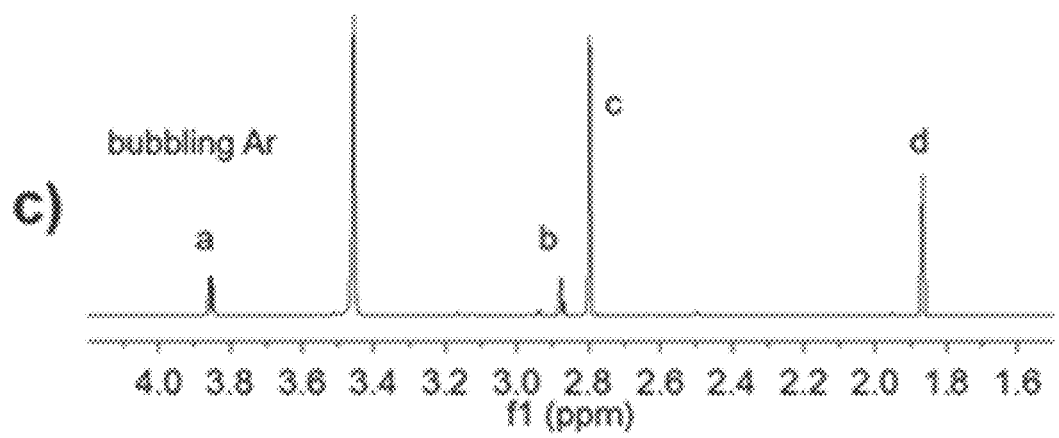

Prior to chemiresistor testing, we performed $^1$H NMR study of N'-propargyl-N,N-dimethylacetamidine (PDAA) to confirm the $CO_2$ reactions with the switchable amidine moiety. FIG. 16A shows the $^1$H NMR spectrum of PDAA in dry DMSO-$d_6$ recorded before the $CO_2$ treatment. Upon bubbling a stream of $CO_2$ through the solution for 2 min in the presence of a few drops of DI-water, all characteristic peaks of PDAA were shifted to downfield indicating protonation by carbonic acid (FIG. 16B). Subsequent bubbling of Ar through the same solution for 2 min reverses the reaction and the peaks shift to their original positions (FIG. 16C). Hence it confirms the reversible switchability of amidine in response to $CO_2$ in the presence of water.

Figure 4A:
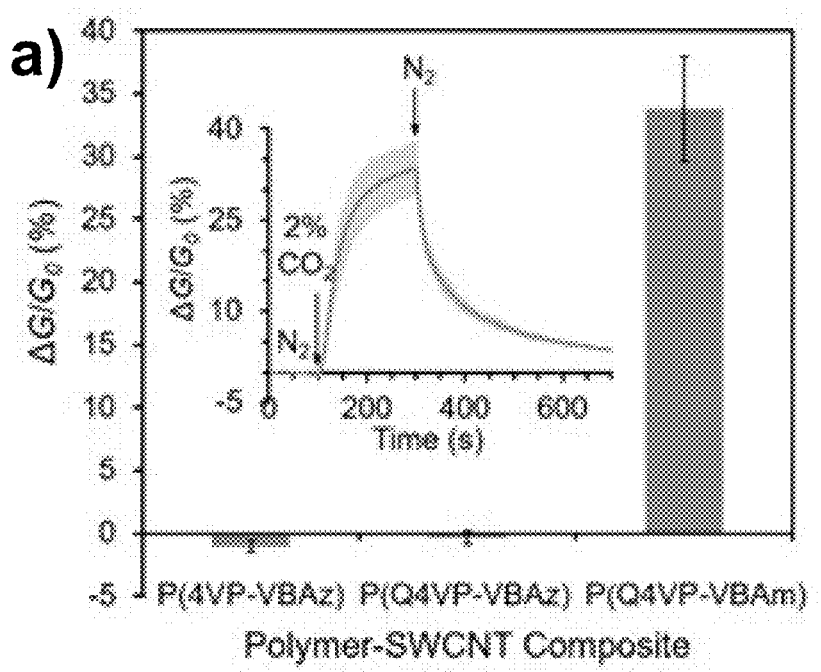
FIGS. 4A-4E depict properties of the devices described herein.
Figure 4B:
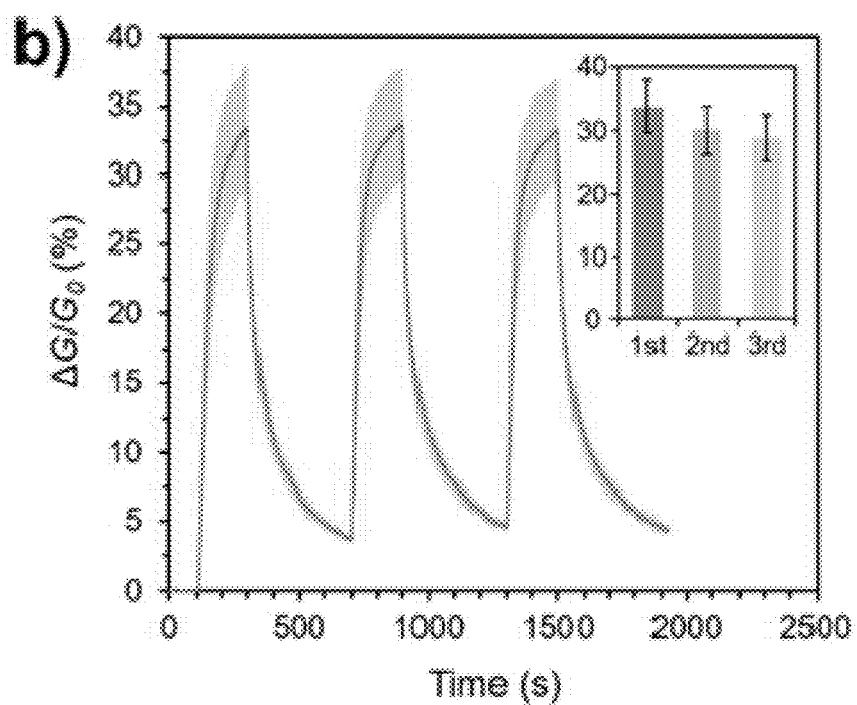
Figure 4C:
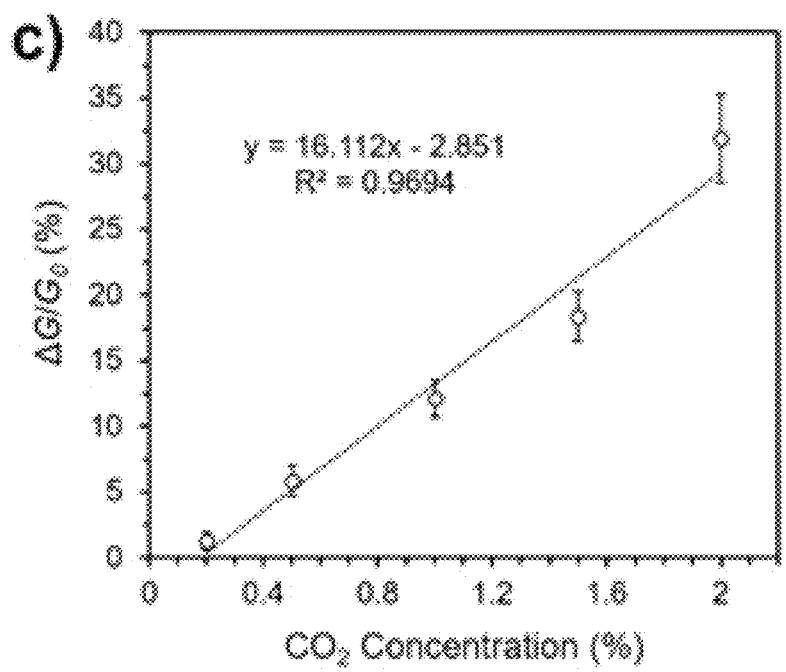
Figure 17:
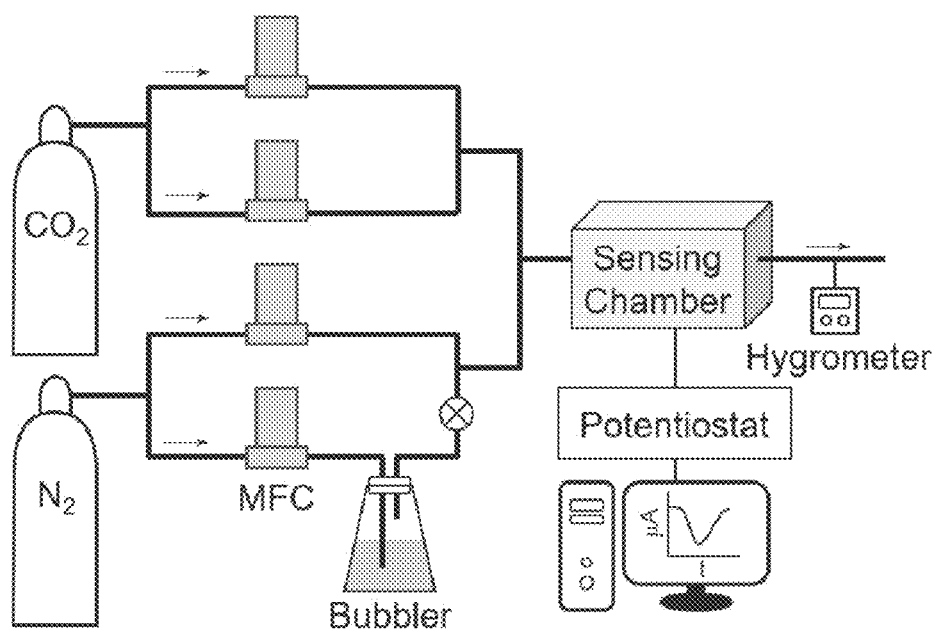
FIG. 17 depicts a schematic of a chemiresistive $CO_2$ sensing set up.
Figure 18:
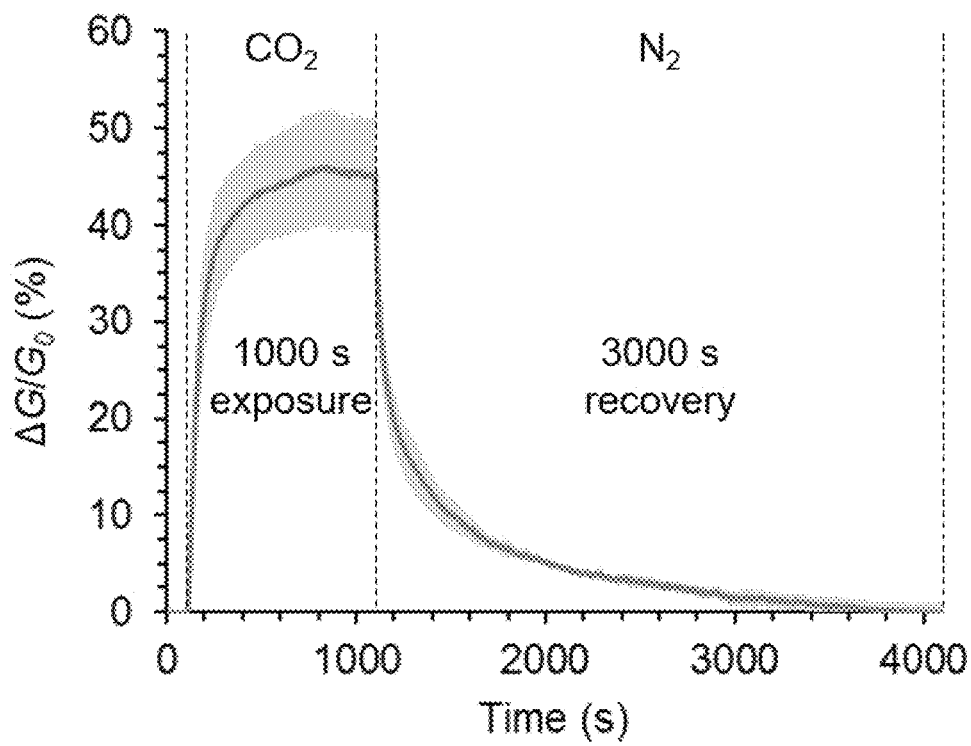
FIG. 18 depicts a graph showing average conductance traces of four P(Q4VP-VBAm)-SWCNT devices in response to 1000 s exposure to 2% $CO_2$ in $N_2$ and subsequent $N_2$ purge for 3000 s (RH 53%). The shaded area indicates the standard deviation (N=4 sensors).
Figure 19:
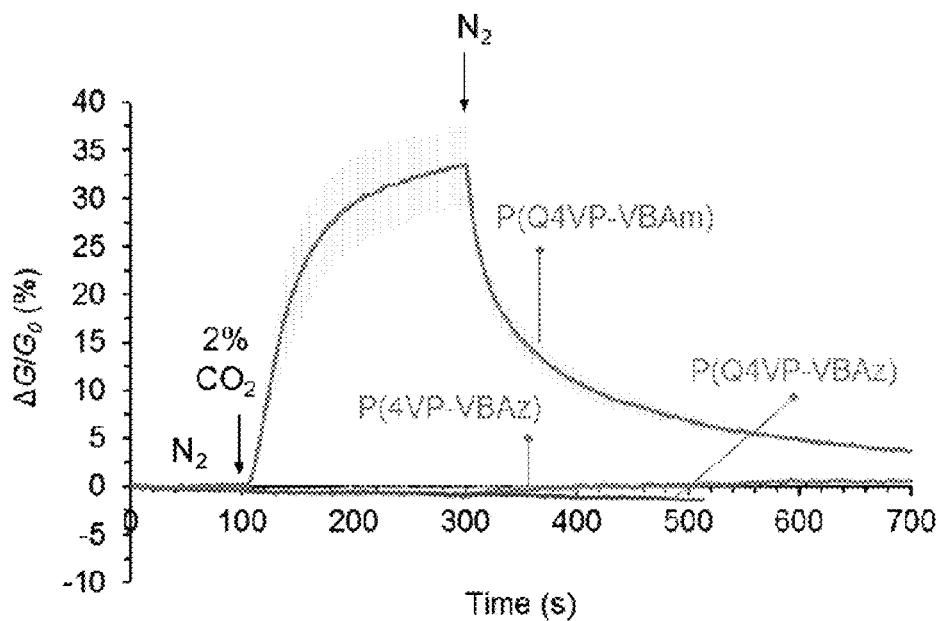
FIG. 19 is a graph depicting average conductance traces of four devices of P(4VP-VBAz)-SWCNT, P(Q4VP-VBAz)-SWCNT and P(Q4VP-VBAm)-SWCNT in response to 200 s exposure to 2% $CO_2$ in $N_2$ (RH 53%). The shaded areas indicate the standard deviation (N=4 sensors).
Figure 20:
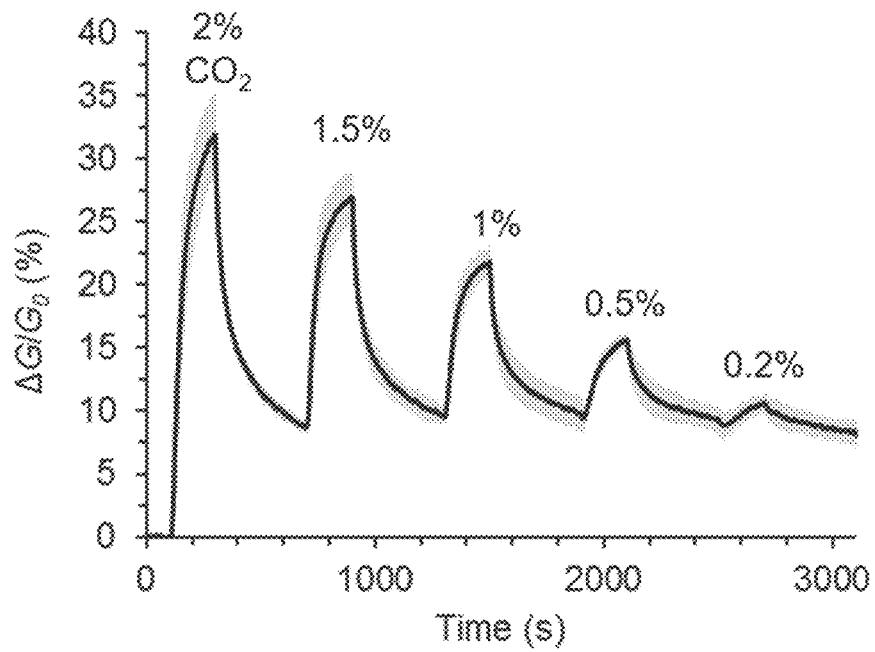
FIG. 20 is a graph depicting average conductance traces of four P(Q4VP-VBAm)-SWCNT devices in response to 200 s exposure to varying concentration of $CO_2$ in $N_2$ at RH 53%. The shaded area indicates the standard deviation (N=4 sensors).

$CO_2$-switchable P(Q4VP-VBAm)-SWCNT chemiresistive sensors were fabricated by spray-coating of the precursor P(4VP-VBAz)-SWCNT on gold electrodes with an interelectrode spacing of 1 mm, followed by sequential quaternization and click reactions as described above. $CO_2$ gas exposure under humidified atmosphere generates amidinium bicarbonates, which results in increasing the density of mobile hole carriers thereby increasing the net conductance of the sensor. Four mass flow controllers (MFCs) were used to deliver a mixture of $CO_2$ in $N_2$ (500 mL/min) to the device and the current was measured with a 0.1 V bias between adjacent devices. A water bubbler was connected between one of the MFCs and the inlet of device's enclosure to adjust humidity of the gas mixture (FIG. 17). FIG. 4A inset shows the average chemiresistive trace of the normalized positive change in current $[\Delta G/G_0(\%)=(I-I_0)/I_0 \times 100\%$, where $I_0$ is initial current] of four devices resulting from the 200 s exposure to 2% $CO_2$ in $N_2$ at relative humidity (RH) of 53% at 21° C. It was found that the P(Q4VP-VBAm)-SWCNT device shows a significant increase in conductance of 33.8±4.2% upon exposure to $CO_2$, which is consistent with the hypothesis described herein. The sensor exhibits reversible responses to $CO_2$ (FIG. 4B). It saturates after about 1000 s exposure of 2% $CO_2$ and nearly full recovery is realized with $N_2$ purging for 3000 s at RH 53% (FIG. 18). The devices fabricated with P(4VP-VBAz)-SWCNT and P(Q4VP-VBAz)-SWCNT showed negligible responses to 2% of $CO_2$ under the same conditions, indicating that the amidine moiety is responsible for the increase in conductance upon $CO_2$ exposure (FIG. 4A and FIG. 19). The responses of P(Q4VP-VBAm)-SWCNT sensors toward 200 s exposure of varying $CO_2$ concentrations from 0.2% to 2% at RH 53% are summarized in FIG. 4C. The calculated theoretical limit of detection for 200 s exposure is 0.03%. FIG. 20 shows averaged conductance trace for these measurements.

Figure 4D:
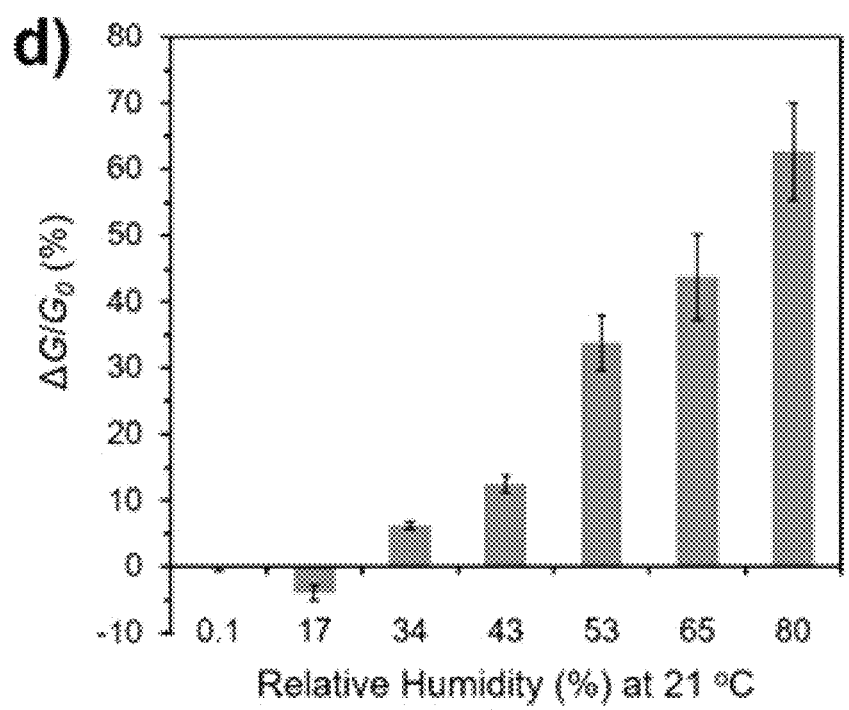
Figure 4E:
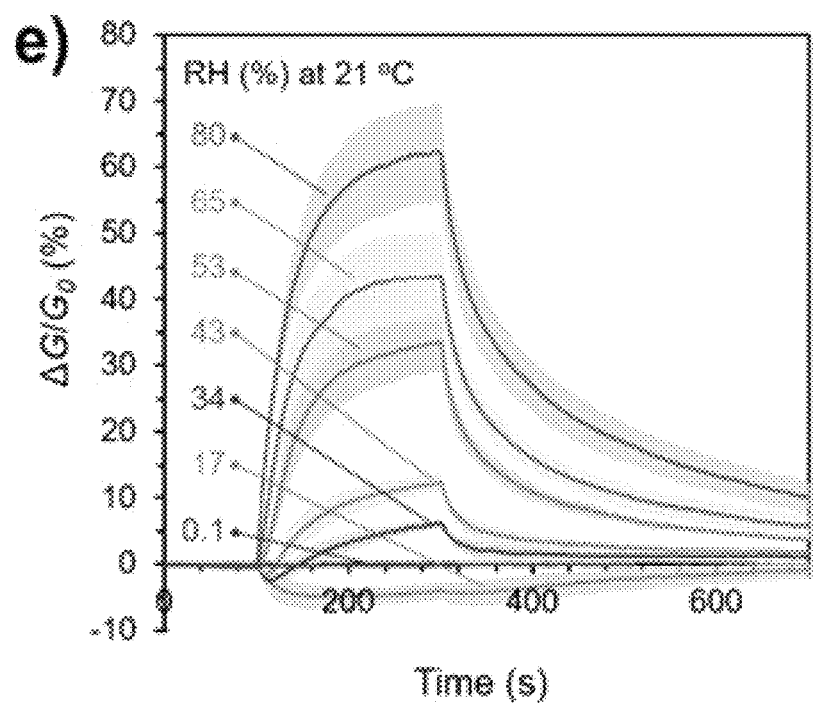
Figure 21:
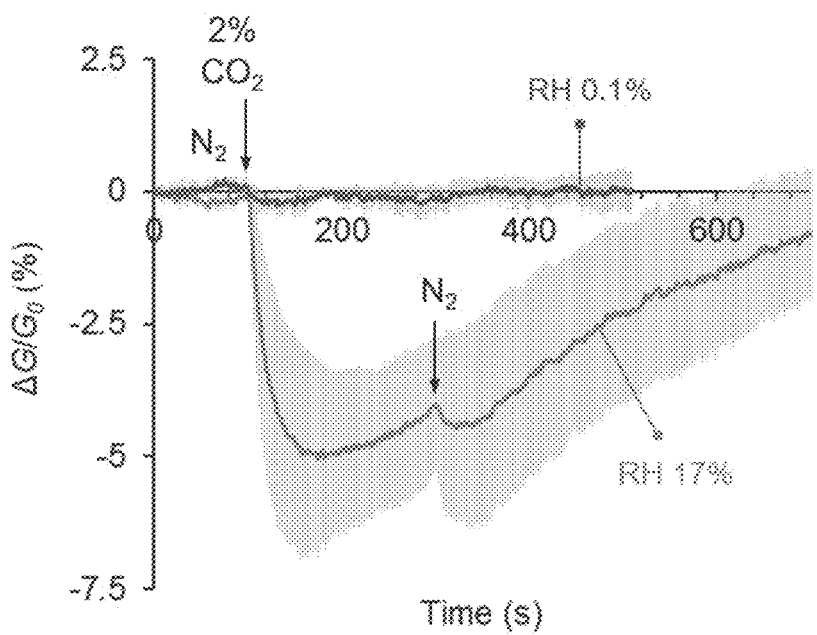
FIG. 21 is a graph depicting average conductance traces of four P(Q4VP-VBAm)-SWCNT devices in response to 200 s exposure to 2% $CO_2$ in $N_2$ at low relative humidity conditions, RH 0.1% and RH 17%. The shaded areas indicate the standard deviation (N=4 sensors).

Water is needed to produce the carbonic acid (FIG. 2A) and the sensitivity of the P(Q4VP-VBAm)-SWCNT device to 2% $CO_2$ at various RH values was evaluated. As shown in FIG. 4D, increasing RH promotes higher responses. The highest response was found to be a conductance change of 62.7±7.2% at RH 80%. There is no response to 2% $CO_2$ under the conditions of dry $N_2$ (RH 0.1%). The corresponding chemiresistive traces of four P(Q4VP-VBAm)-SWCNT devices are shown in FIG. 4E. At a low RH of 17%, the overall conductance of the device was found to decrease slightly upon 200 s exposure to 2% $CO_2$ (−3.9±1.1%). In FIG. 21, an enlarged plot for the conductance trace of the P(Q4VP-VBAm)-SWCNT device at RH 17% shows a rapid decrease in conductance for the first 70 s of $CO_2$ exposure followed by a gradual increase over the remaining exposure time. This signal also reverts to the initial value when purged with the $CO_2$ free carrier gas. This result suggests that there may be minor competitive interactions between the amidinium bicarbonates and the pyridinium ions. Presumably at low RH there are ionic associations that prevent carrier mobility that are not present with higher degrees of hydration.

Figure 5A:
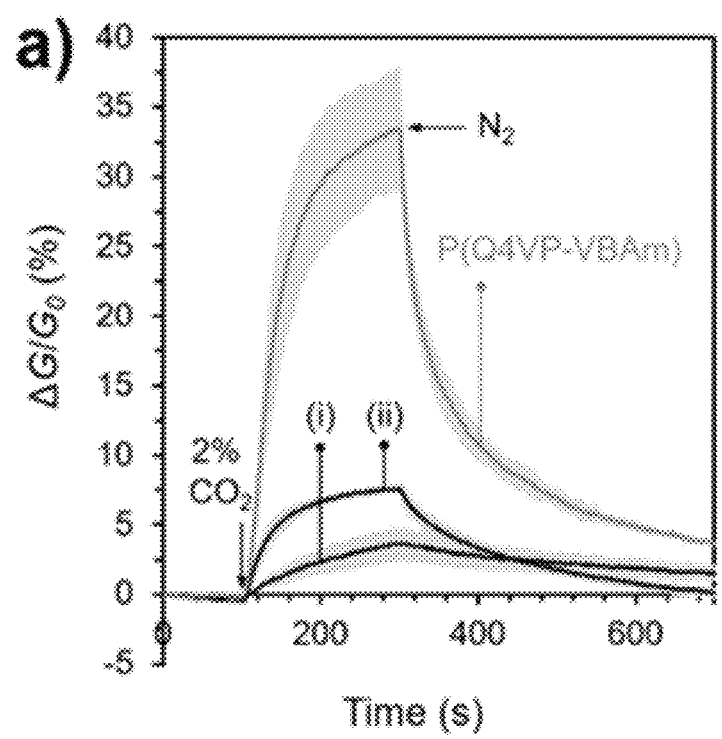
FIGS. 5A-5D are graphs depicting device performance.
Figure 5B:
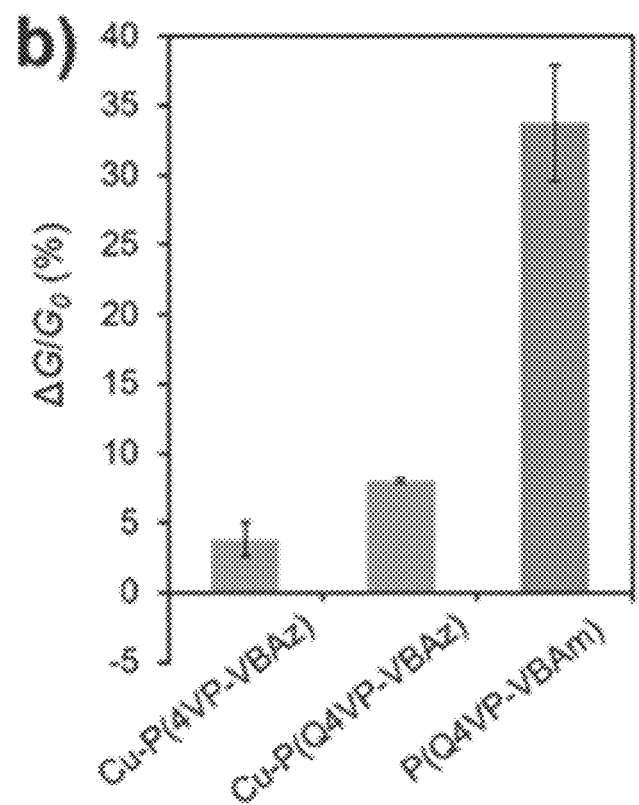
Figure 5C:
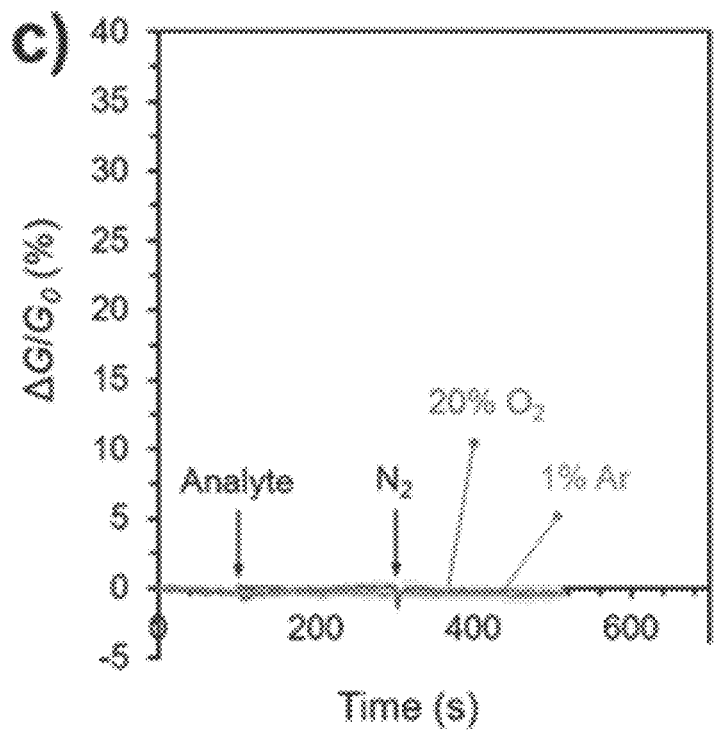
Figure 5D:
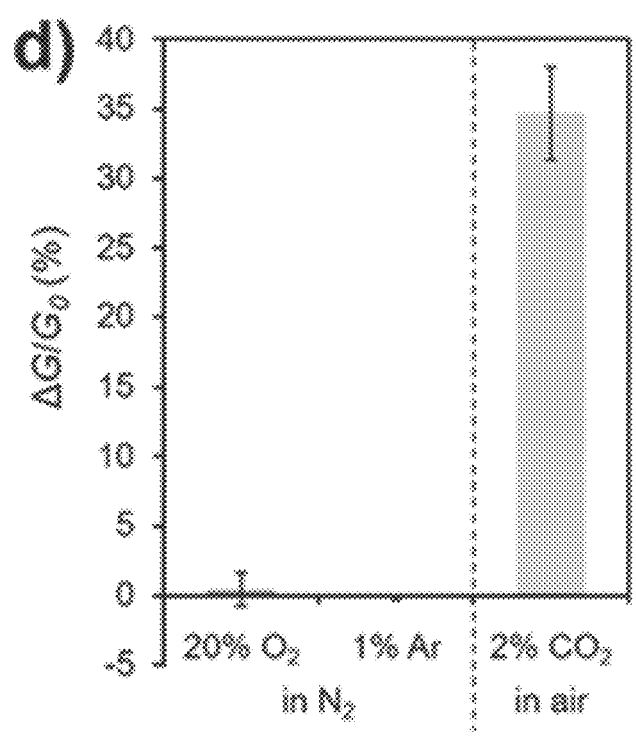
Figure 6:
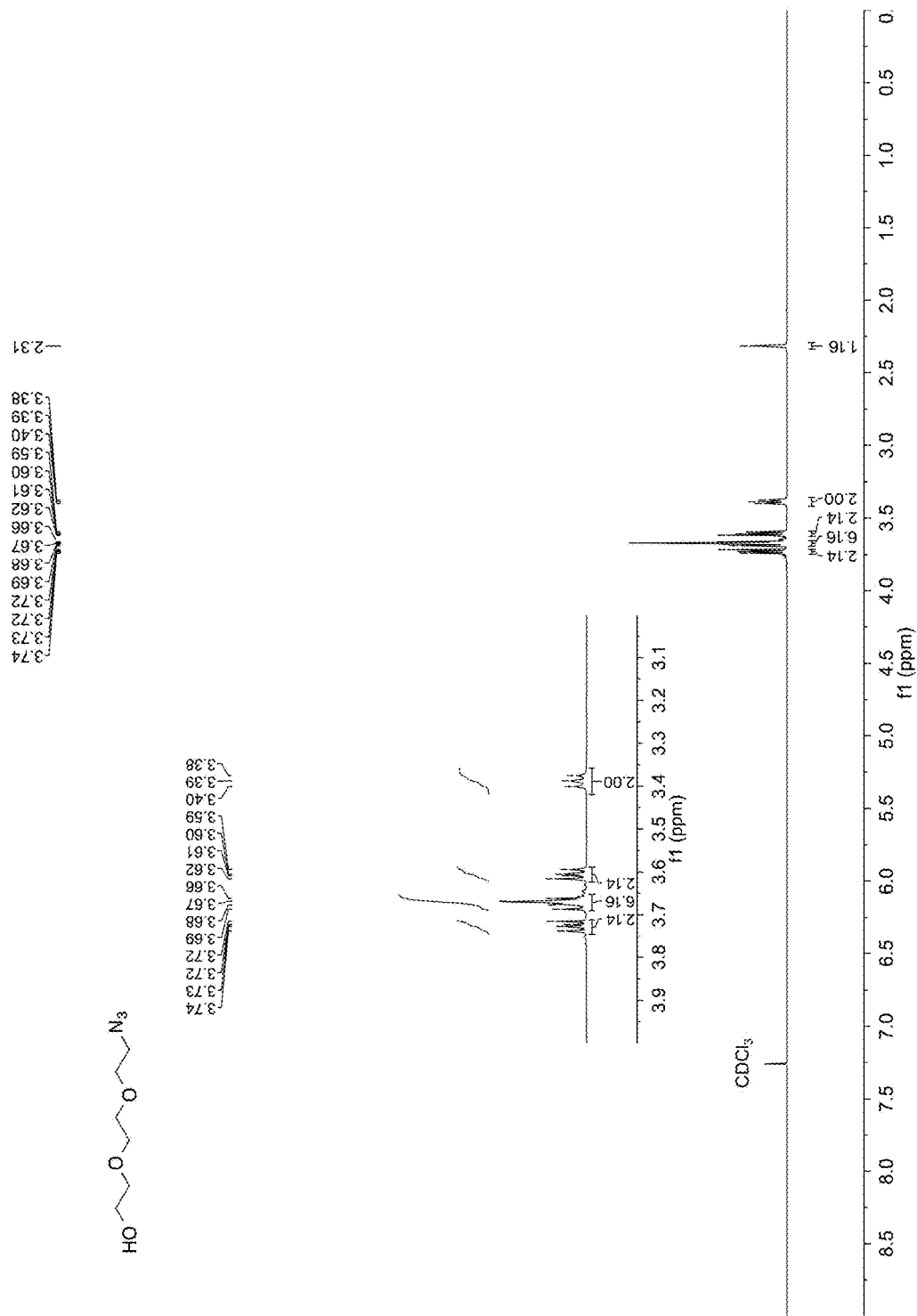
FIG. 6 is a $^1$H NMR spectrum of 2-(2-(2-Azidoethoxy)ethoxy)ethanol (1).
Figure 7:
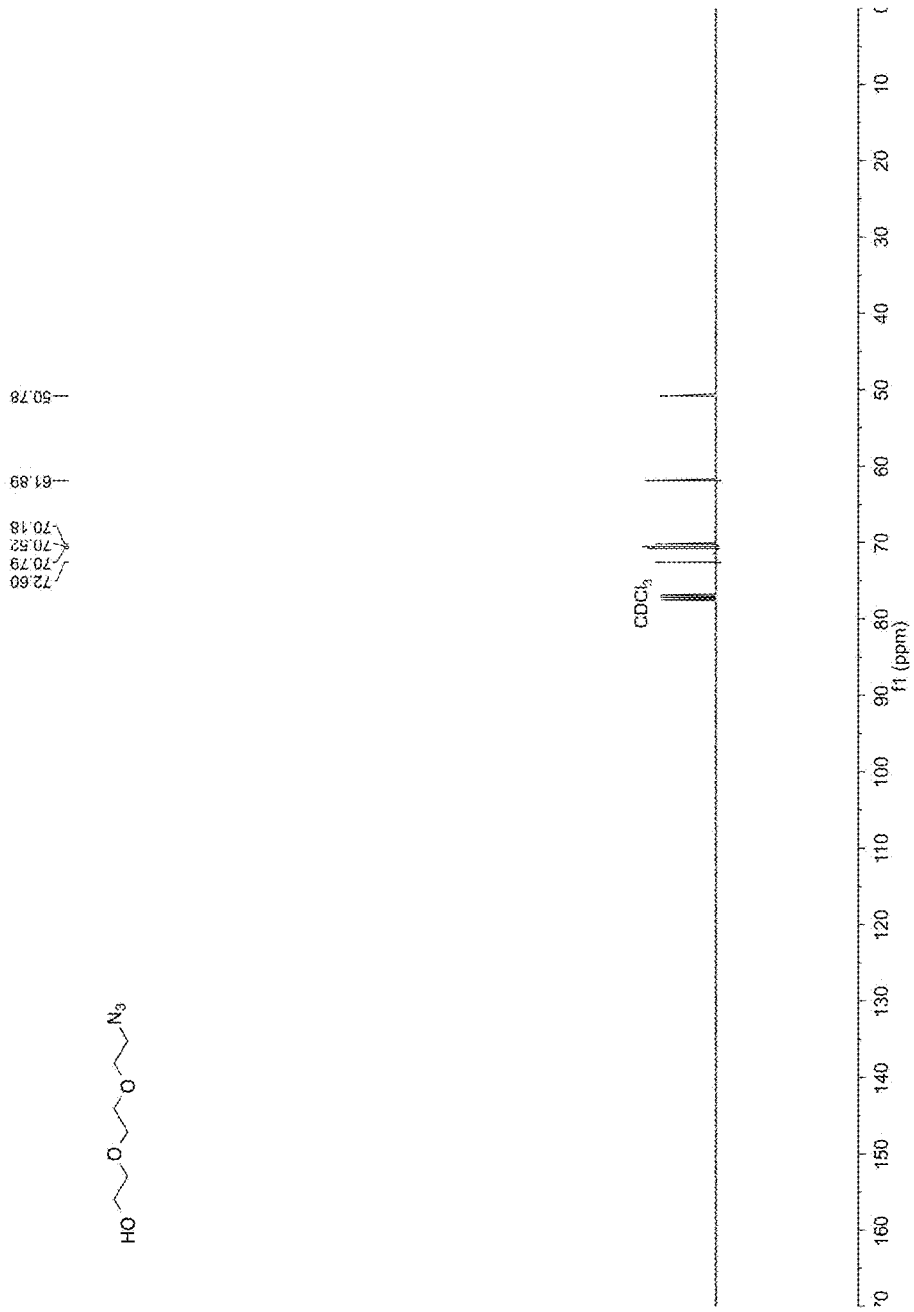
FIG. 7 is a $^{13}$C NMR spectrum of 2-(2-(2-Azidoethoxy)ethoxy)ethanol (1).
Figure 8:
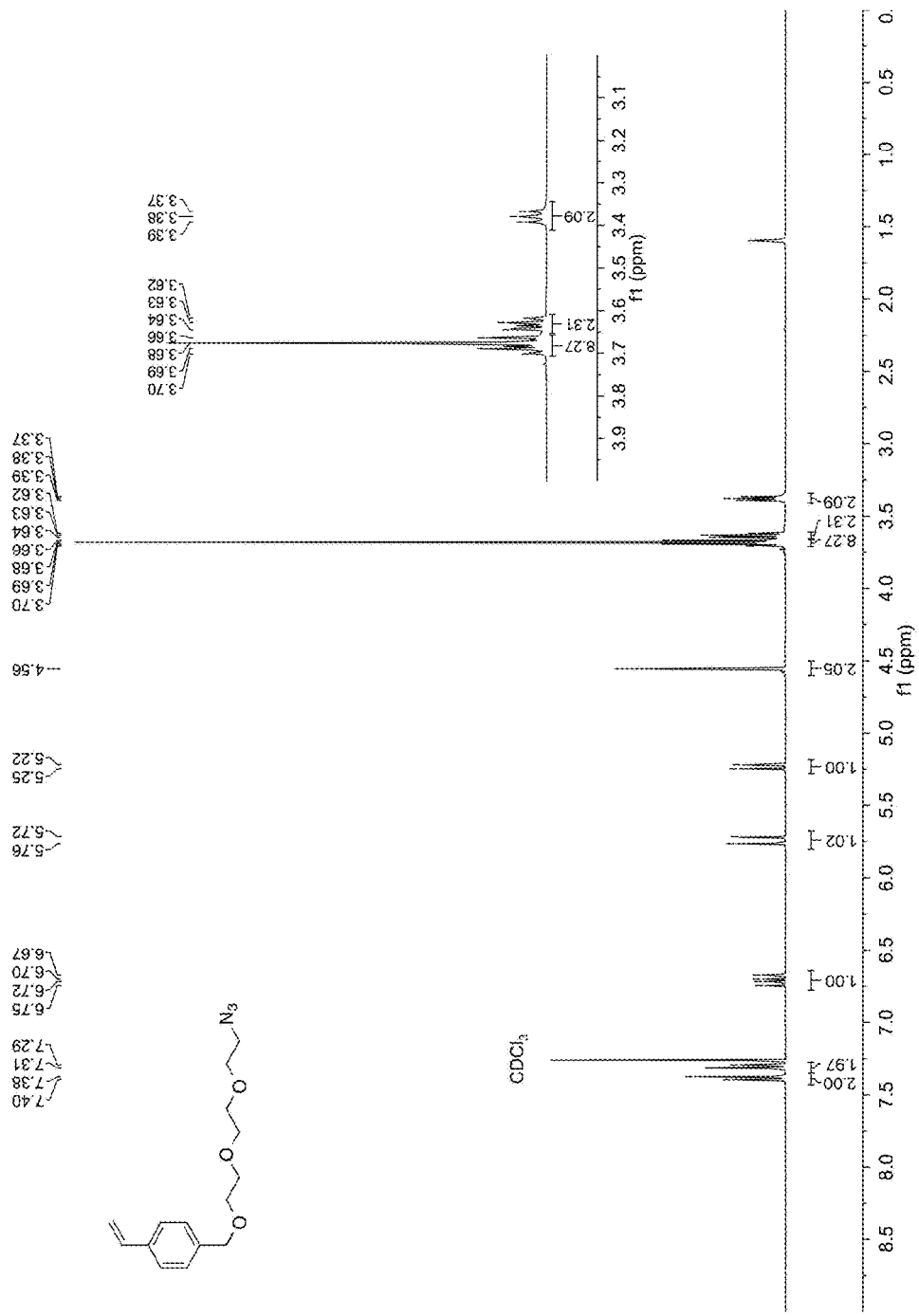
FIG. 8 is a $^1$H NMR spectrum of 1-((2-(2-(2-Azidoethoxy)ethoxy)ethoxy)methyl)-4-vinylbenzene (2).
Figure 9:
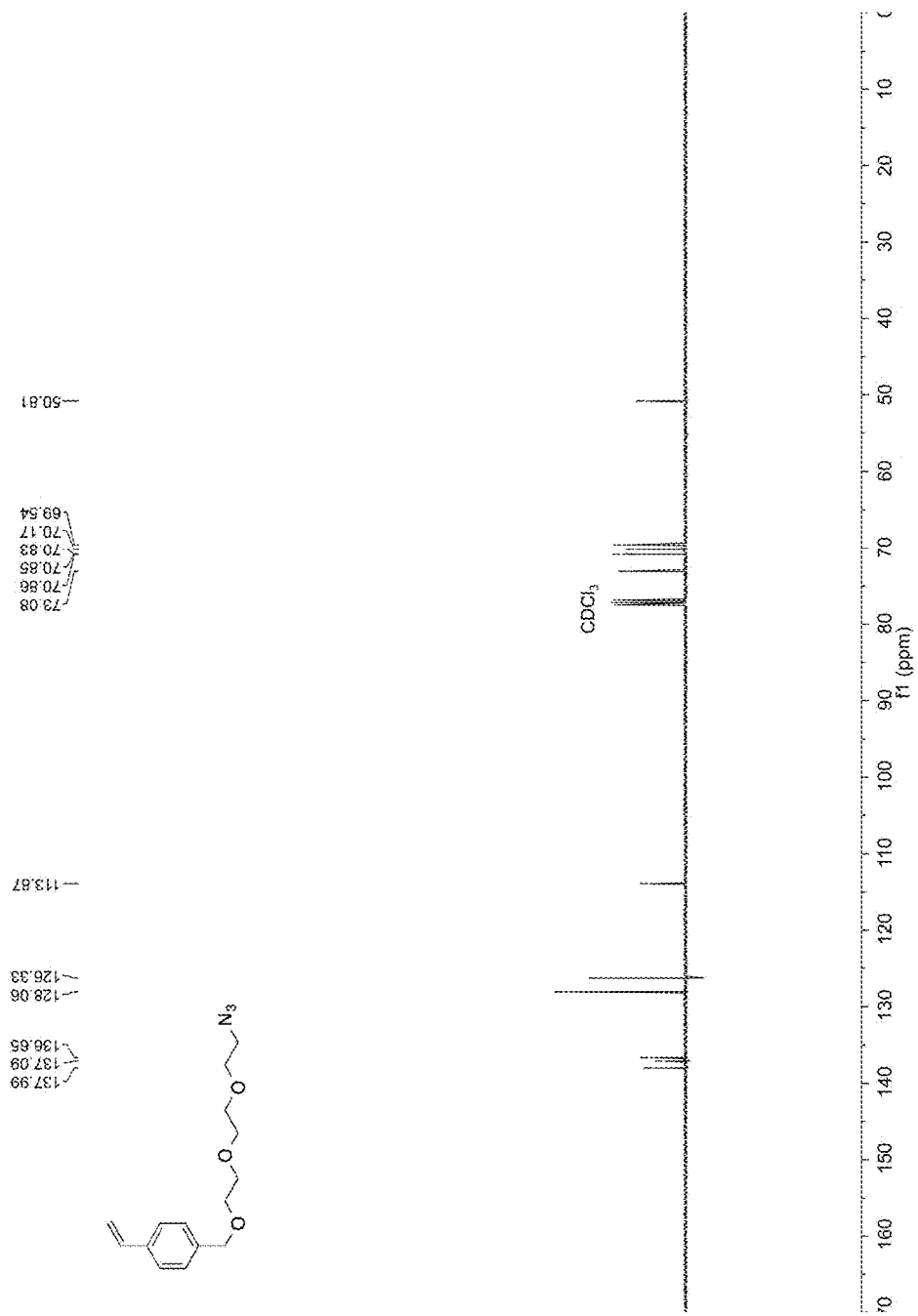
FIG. 9 is a $^{13}$C NMR spectrum of 1-((2-(2-(2-Azidoethoxy)ethoxy)ethoxy)methyl)-4-vinylbenzene (2).
Figure 10:
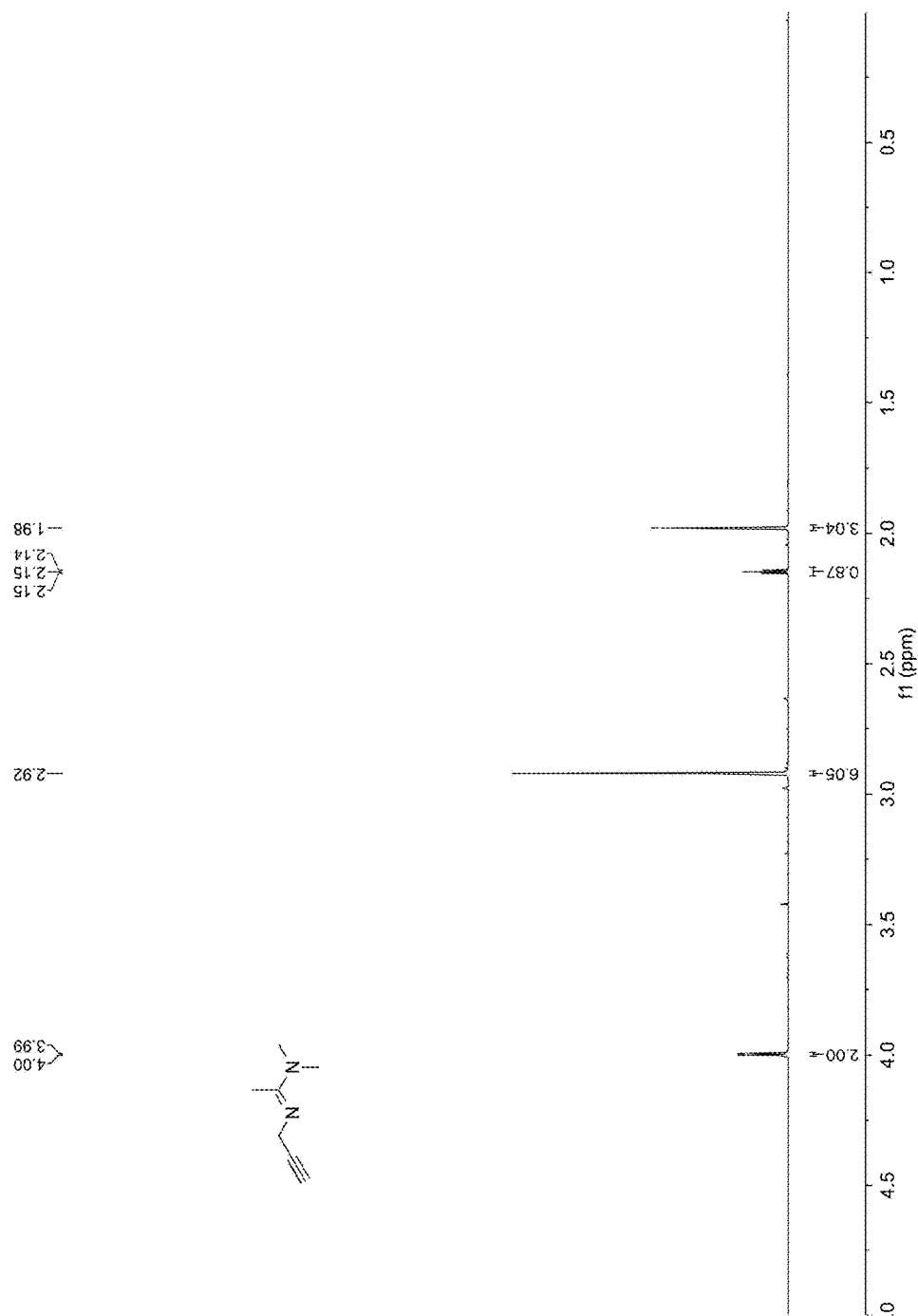
FIG. 10 is a $^1$H NMR spectrum of N'-Propargyl-N,N-dimethylacetamidine (PDAA).
Figure 11:
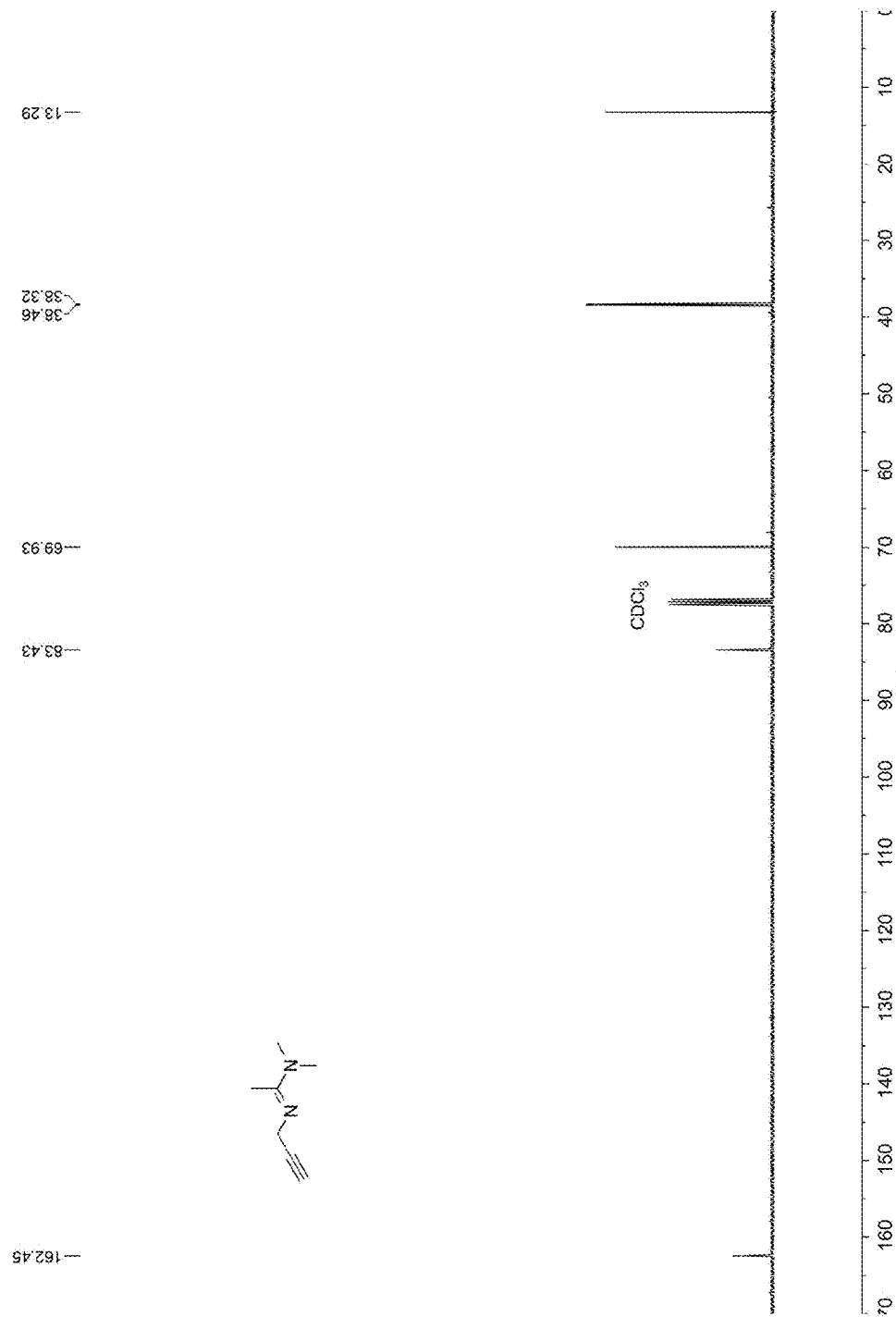
FIG. 11 is a $^{13}$C NMR spectrum of N'-Propargyl-N,N-dimethylacetamidine (PDAA).
Figure 22A:
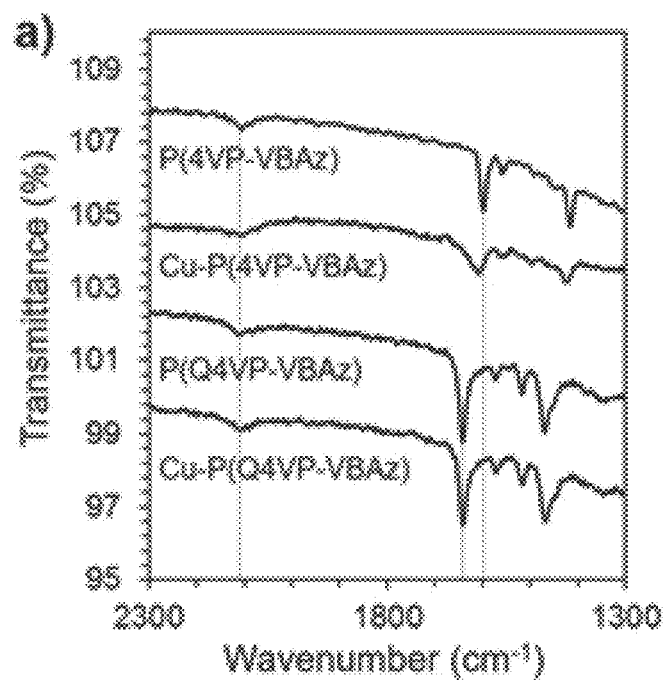
FIGS. 22A-22E are graphs depicting spectral data for the compositions described.
Figure 22B:
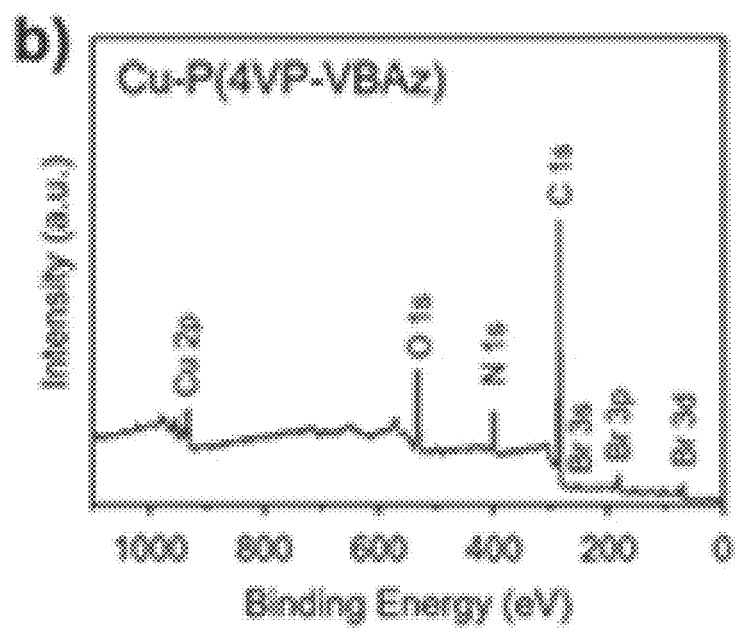
Figure 22C:
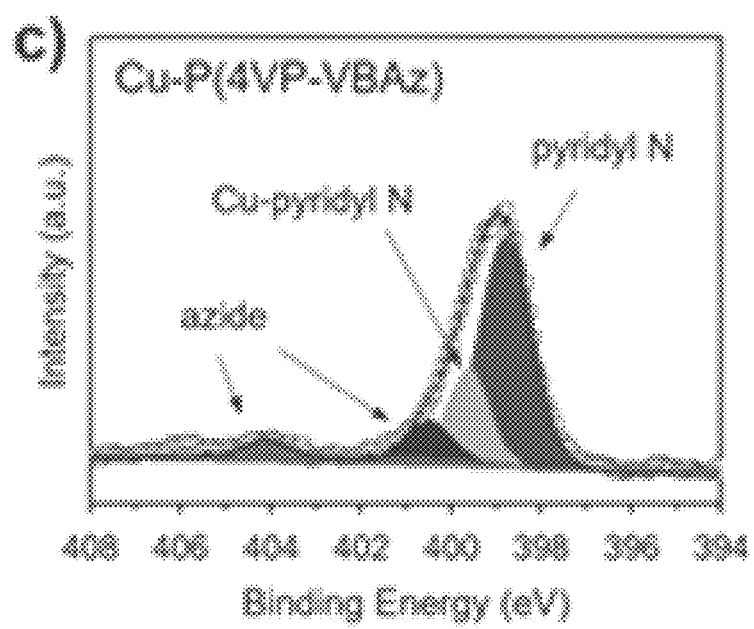
Figure 22D:
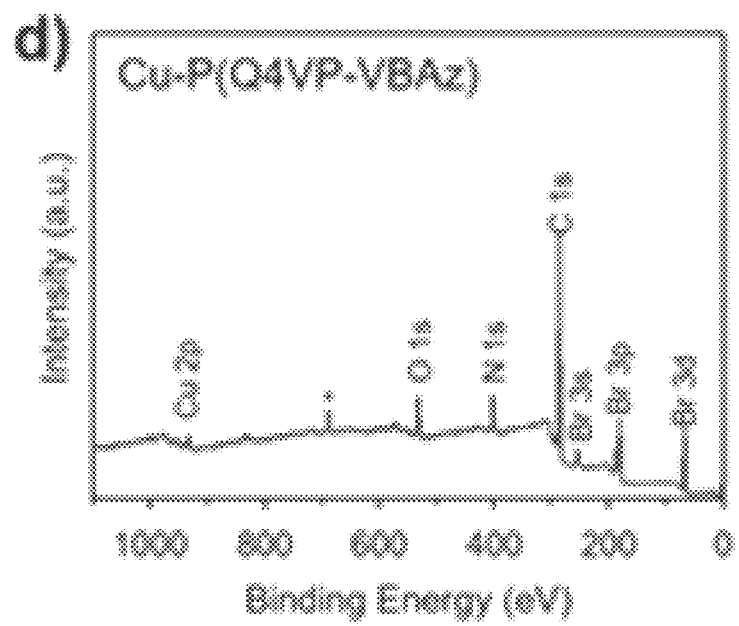
Figure 22E:
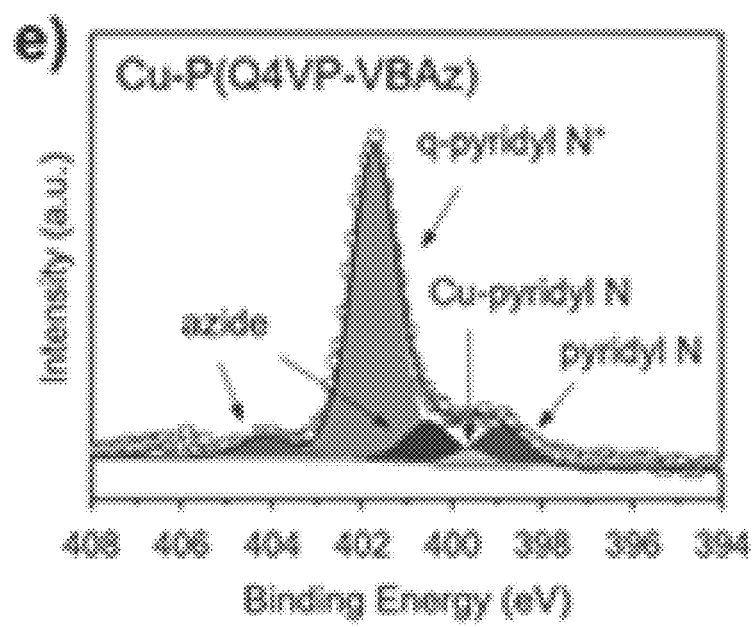
Figure 23:
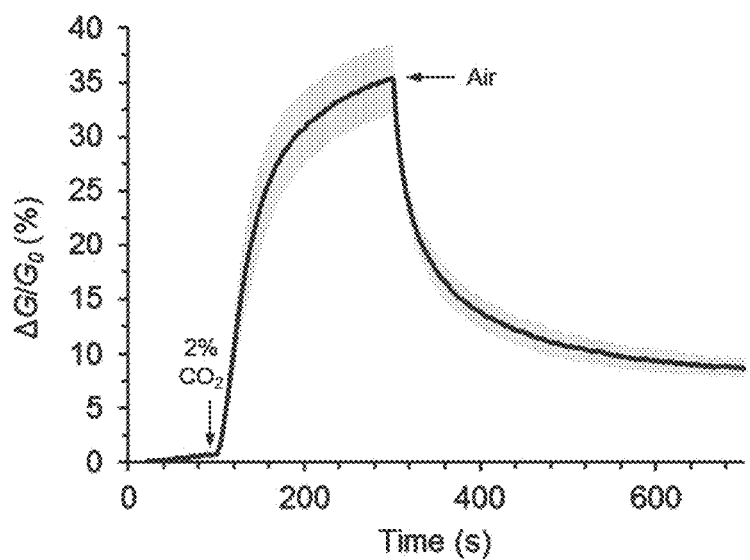
FIG. 23 depicts a graph showing average conductance traces of four devices of P(Q4VP-VBAm)-SWCNT in response to 200 s exposure to 2% $CO_2$ in air (RH 53%). The shaded area indicates the standard deviation (N=4 sensors, P=0.14 by a paired two-sample Student's t-test between devices tested in response to 200 s exposure to 2% $CO_2$ in $N_2$ and air at RH 53%).

As mentioned previously, 1.2 at % of the residual Cu ions were observed by XPS in the final P(Q4VP-VBAm)-SWCNT composite (FIG. 15C), and with oxygen the oxidation state is likely Cu(II). To determine if residual Cu effects the sensing performance, we prepared control devices based on P(4VP-VBAz)-SWCNT and P(Q4VP-VBAz)-SWCNT that lack the amidine moiety and were doped with Cu(I) ions. The pyridyl nitrogen of P(4VP-VBAz)-SWCNT binds the Cu ions, which is observed by the shift and broadening of the pyridyl C=N stretching band from 1598 to 1608 cm$^{-1}$ in the FTIR spectrum (FIG. 22A). Incorporation of 2.4 at % Cu into the P(4VP-VBAz)-SWCNT device was also evidenced by XPS spectra shown in FIGS. 22B and 22C. The additional band at 399.6 eV in the N 1 s XPS spectrum is attributable to the Cu-incorporated pyridyl N. No appreciable changes were observed in the FTIR spectrum of Cu—P(Q4VP-VBAz)-SWCNT (FIG. 22A) because of the quaternized pyridine. A trace of Cu ion (0.9 at %) was found in its XPS spectra shown in FIGS. 22D and 22E. In FIG. 5A and FIG. 5B, control experiments with the Cu—P(4VP-VBAz) and Cu—P(Q4VP-VBAz) showed 3.8±1.2 and 8.1±0.1% conductance changes, respectively, upon 200 s exposure to 2% $CO_2$ at RH 53%. These responses are likely the result of interactions between the $CO_2$ generated carbonic acids and the Cu ions bound to the polymer-SWCNT composites, which generate electron depletion at the SWCNT surface and increase the hole carrier density. Regardless, sensors fabricated with P(Q4VP-VBAm)-SWCNT showed much higher responses to $CO_2$ than those with Cu—P(4VP-VBAz)-SWCNT and Cu—P(Q4VP-VBAz)-SWCNT under the same experimental conditions. Hence the amidine in P(Q4VP-VBAm)-SWCNT is responsible for the higher sensing performance. P(Q4VP-VBAm)-SWCNT sensors can have high selectivity for $CO_2$ and do not display significant response to 20% $O_2$ or 1% Ar introduced into the humidified (RH 53%) $N_2$ carrier gas (FIG. 5C and FIG. 5D). We have also tested the sensors under air at RH 53% (FIG. 5D and FIG. 23). When compared with the response in humid $N_2$, the P(Q4VP-VBAm)-SWCNT sensor exhibits a similar tendency of conductance change of 34.7±3.5%. A statistical analysis by Student's t-test shows no significant difference between the sensors tested in $N_2$ and air at RH 53% (FIG. 23). The sensor again responds reversibly to 200 s exposure of 2% $CO_2$ in humid air.

Surface-immobilized $CO_2$ sensor based on SWCNT composites containing a $CO_2$-switchable amidine-tethered copolymer have been developed using a precursor approach for the sensor device fabrication wherein the surface of the precursor polymer P(4VP-VBAz)-SWCNT composites is first quaternized with bromoethane and then the amidine moieties are subsequently introduced to produce $CO_2$-switchable P(Q4VP-VBAm)-SWCNT composites via a click reaction. Sensors fabricated with P(Q4VP-VBAm)-SWCNT showed a substantial increase in conductance (~34%) upon 200 s exposure to 2% $CO_2$ in $N_2$ at RH 53% at 21° C., which resulted from the generated amidinium bicarbonates in the polymer wrapping. The amidinium moiety reversibly converts back into the amidine when purged with $N_2$. Sensor performance was demonstrated at various RH values and $CO_2$ concentrations, and its selectivity to $CO_2$ over the other atmospheric gases. The sensor can detect $CO_2$ in humid air. The amidine is introduced in the last step of sensor fabrication and similar surface click reactions can be used to produce sensors for other target analytes by proper choice of functionalizing acetylenes.

EXAMPLES

General Materials

All chemicals, reagents and SWCNTs (CoMoCAT SWCNTs with an average diameter of 0.82 nm, >89% carbon basis, >99% as carbon nanotubes, lot #: MKBP333V) were purchased from Sigma-Aldrich and used without additional purification, unless noted otherwise. 2,2'-Azobis(2-methylpropionitrile) (AIBN) was recrystallized from methanol and stored in the dark at 4° C. 4-Vinylpyridine (4VP) was purified by passing through a column of neutral alumina, and then vacuum distilled from $CaH_2$. The purified 4VP was stored at −20° C. N,N-Dimethylformamide (DMF) was vacuum distilled from $CaH_2$. Deuterated solvents for NMR spectroscopy was purchased from Cambridge Isotope Laboratories, Inc. 3-Bromopropyltrichlorosilane and bromoethane (98%) were purchased from Gelest and Alfa Aesar, respectively. Tris[(1-benzyl-1H-1,2,3-triazol-4-yl)methyl]amine was purchased from TCI America. Cylinders of $CO_2$ (99.999%) and $O_2$ (99.994%) were purchased from Airgas.

Characterization $^1H$ and $^{13}C$ NMR spectra were acquired by Bruker Avance Spectrometer operating at 400 MHz and 101 MHz for $^1H$ and $^{13}C$, respectively. Chemical shifts are referenced to residual NMR solvent peaks ($CDCl_3$: 7.24 ppm for $^1H$ and 77.16 for $^{13}C$, DMSO-$d_6$: 2.50 ppm for $^1H$). The gel permeation chromatography (GPC) was carried out with Agilent 1260 LC system running at 60° C. with 0.025 M LiBr solution in DMF as eluent. A Wyatt Optilab T-rEX refractometer and a Wyatt DAWN HELEOS-II multi-angle static light scattering detector were used to collect signals and the data were analyzed using Astra v.6.1.6.5 software. UV-vis-NIR absorption spectra were obtained using an Agilent Cary 5000 spectrophotometer. ATR-FTIR spectra were obtained using a Thermo Scientific Nicolet 6700 FTIR with a Ge crystal for ATR. Raman spectra were collected with excitation at 633 nm laser using a Horiba LabRAM HR800 Raman spectrometer. X-ray photoelectron spectroscopy (XPS) was performed with a Thermo Scientific K-Alpha$^+$ XPS spectrometer.

Synthesis Procedures

Synthesis of 2-(2-(2-Azidoethoxy)ethoxy)ethanol (1)

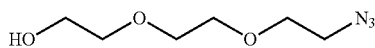

2-(2-(2-Azidoethoxy)ethoxy)ethanol was synthesized according to a previously reported method (see, for example, Yamaguchi, T.; Asanuma, M.; Nakanishi, S.; Saito, Y.; Okazaki, M.; Dodo, K.; Sodeoka, M. Turn-On Fluorescent Affinity Labeling Using a Small Bifunctional o-Nitrobenzoxadiazole Unit. Chem. Sci. 2014, 5, 1021-1029, which is incorporated by reference in its entirety). To a solution of 2-(2-(2-chloroethoxy)ethoxy)ethanol (5.00 g, 29.65 mmol) in water (11 mL) was added sodium azide (3.86 g, 59.30 mmol). The mixture was stirred at 75° C. for 15 h. The solvent was removed under reduced pressure. Diethyl ether was added, and then the precipitate was removed by filtration. The filtrate solution was evaporated under reduced pressure to yield a colorless liquid (5.09 g, 98%). $^1H$ NMR (400 MHz, $CDCl_3$): δ 3.75-3.70 (m, 2H), 3.69-3.65 (m, 6H), 3.63-3.59 (m, 2H), 3.42-3.36 (m, 2H), 2.31 (s, 1H). $^{13}C$ NMR (101 MHz, $CDCl_3$): δ 72.60, 70.79, 70.52, 70.18, 61.89, 50.78.

Synthesis of 1-((2-(2-(2-Azidoethoxy)ethoxy)ethoxy)methyl)-4-vinylbenzene (2)

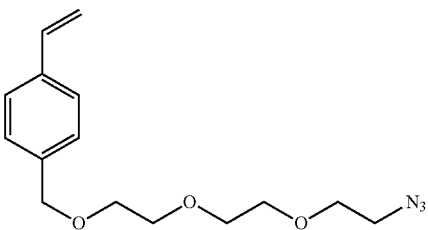

To a solution of 4-vinylbenzyl chloride (2.96 g, 19.38 mmol) in dry THF (30 mL) under argon was added sodium hydride (0.70 g, 29.07 mmol) in an ice water bath, and the mixture was stirred for 2 h. 1 (5.09 g, 29.07 mmol) was then added to the mixture. The reaction mixture was allowed to reach room temperature and stirred for 15 h. The solvent was removed under reduced pressure. The mixture was then diluted with DCM, and washed with brine and water. The organic layer was dried over anhydrous $MgSO_4$, filtered, and concentrated under vacuum. The crude compound was further purified by silica gel column chromatography using 98:2 DCM/MeOH to yield a colorless liquid (3.69 g, 65%). $^1H$ NMR (400 MHz, $CDCl_3$): δ 7.39 (d, J=8.0 Hz, 2H), 7.30 (d, J=8.4 Hz, 2H), 6.71 (dd, J=17.6, 10.9 Hz, 1H), 5.74 (d, J=18.5 Hz, 1H), 5.23 (d, J=11.8 Hz, 1H), 4.56 (s, 2H), 3.71-3.66 (m, 8H), 3.65-3.61 (m, 2H), 3.41-3.34 (m, 2H). $^{13}C$ NMR (101 MHz, $CDCl_3$): δ 137.99, 137.09, 136.65, 128.06, 126.33, 113.87, 73.08, 70.86, 70.85, 70.83, 70.17, 69.54, 50.81. HRMS (ESI) m/z calculated for $C_{15}H_{21}N_3O_3$ $[M+NH_4]^+$: 309.1921, found 309.1921.

Synthesis of P(4VP-VBAz)

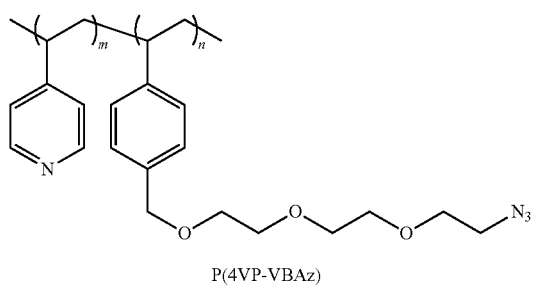

P(4VP-VBAz)

The polymer synthesis was performed in flame-dried flasks under an inert atmosphere with dry argon using standard Schlenk techniques. 4-Vinylpyridine (1.00 g, 9.51 mmol), 2 (0.31 g, 1.06 mmol), AIBN (18.1 mg, 0.11 mmol) and DMF (2.0 mL) were added into a flame-dried Schlenk flask with a stirrer bar, and then degassed by several freeze-thawing cycles. The mixture was stirred at 60° C. for 15 h. After quenching the reaction by cooling the flask, the polymer was precipitated in cold diethyl ether (200 mL). The polymer was re-dissolved in a small amount of methanol and then precipitated in cold diethyl ether. After the three cycles of dissolving-precipitation, the obtained pale yellow powder was dried under vacuum (0.66 g, 50%). $^1H$ NMR (400 MHz, DMSO-$d_6$): δ 8.29-7.97 (brs, 18H), 7.26-6.17

(brs, 22H), 4.39 (s, 2H), 3.65-3.27 (brs, 12H), 2.28-1.04 (brs, 30H). DMF-GPC: $M_n$=39.43 kg/mol, D=1.92.

Synthesis of N'-Propargyl-N,N-dimethylacetamidine (PDAA)

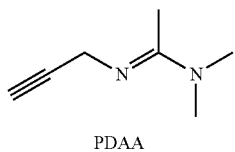

PDAA

PDAA was synthesized according to a previously reported method with slight modifications (see, Guo, Z.; Feng, Y.; He, S.; Qu, M.; Chen, H.; Liu, H.; Wu, Y.; Wang, Y. $CO_2$-Responsive "Smart" Single-Walled Carbon Nanotubes. Adv. Mater. 2013, 25, 584-590; and Harjani, J. R.; Liang, C.; Jessop, P. G. A Synthesis of Acetamidines. J. Org. Chem. 2011, 76, 1683-1691, each of which is incorporated by reference in its entirety). To a stirring solution of N,N-dimethylacetamide dimethyl acetal (0.91 g, 21.80 mmol) and dimethyl amine (18.19 mL of 2 M solution in THF, 36.32 mmol) under argon was added propargyl amine (1.00 g, 18.16 mmol) dropwise. The mixture was stirred at room temperature for 15 h. The solvent and byproducts were removed under reduced pressure to yield a dark red liquid (quantitative). The resulting PDAA was kept under Ar. $^1$H NMR (400 MHz, $CDCl_3$): δ 4.00 (d, J=2.6 Hz, 2H), 2.92 (s, 6H), 2.16-2.13 (m, 1H), 1.98 (s, 3H). $^{13}$C NMR (101 MHz, $CDCl_3$): δ 162.45, 83.43, 69.93, 38.46, 38.32, 13.29.

Synthesis of P(VBAz)

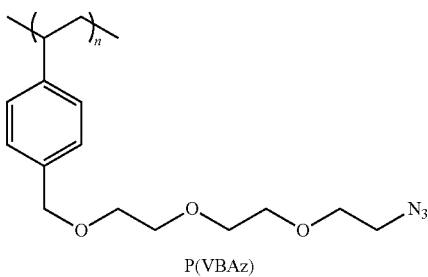

P(VBAz)

The polymer synthesis was performed in flame-dried flasks under an inert atmosphere with dry argon using standard Schlenk techniques. 2 (0.68 g, 2.34 mmol), AIBN (3.78 mg, 0.02 mmol) and DMF (1.0 mL) were added into a flame-dried Schlenk flask with a stirrer bar, and then degassed by several freeze-thawing cycles. The mixture was stirred at 60° C. for 15 h. After quenching the reaction by cooling the flask, the polymer was precipitated in cold diethyl ether (200 mL). The polymer was re-dissolved in a small amount of dichloromethane and then precipitated in cold diethyl ether. After the two cycles of dissolving-precipitation, the obtained gel-like powder was dried under vacuum (0.12 g, 18%). After drying, the resulting polymer is insoluble in common organic solvents. ATR-FTIR: 2863 ($v_{C-H}$), 2103 ($v_{N=N}$), 1096 ($v_{C-O}$) $cm^{-1}$.

Chemiresistor Device Fabrication

Preparation of P(4VP-VBAz) Dispersion.

To a solution of P(4VP-VBAz) (50 mg) in DMF (10 mL) was added SWCNT (5 mg), and then the resulting mixture was sonicated for 1 h in an ultrasonic bath (Branson, 3510) chilled with ice and then allowed to reach room temperature. Subsequently, the suspension was centrifuged for 30 min at 15,000 g (Eppendorf Centrifuge 5804) and allowed to stand overnight undisturbed. The isolated supernatant was directly used for the device fabrication via spray coating unless otherwise indicated.

Preparation of Surface-Immobilized $CO_2$ Sensor Platforms.

Following literature procedures with slight modifications, 0.3 mL of P(4VP-VBAz)-SWCNT dispersion was spray-coated on gold electrodes with an interelectrode spacing of 1 mm thermally evaporated on a glass substrate functionalized with 3-bromopropyltrichlorosilane (see, Yoon, B.; Liu, S. F.; Swager, T. M. Surface-Anchored Poly(4-vinylpyridine)—Single-Walled Carbon Nanotube—Metal Composites for Gas Detection. Chem. Mater. 2016, 28, 5916-5924, which is incorporated by reference in its entirety). To avoid thermal degradation of the azide group of the polymer, the dispersion was sprayed onto the substrate placed on a 130° C. hot plate within 1 h, and then the substrate was thermally annealed at 60° C. overnight, followed by sonication in pure DMF for 1 min to remove excess polymers and non-immobilized P(4VP-VBAz)-SWCNT composites. The device was rinsed with pure DMF, and dried under a stream of $N_2$. The subsequent reaction with bromoethane to form quaternized P(Q4VP-VBAz)-SWCNTs was carried out by soaking the device in the bromoethane solution in acetonitrile (1:10, v/v) at 60° C. for 18 h, sonicated in pure acetonitrile for 1 min to remove excess bromoethane, rinsed with pure acetonitrile, and then dried under a stream of $N_2$. The copper(I)-catalyzed azide-alkyne cycloaddition between PDAAs and pendant azide groups at the surface of SWCNT composites was performed by soaking the quaternized P(Q4VP-VBAz)-SWCNT composite substrate into a 5 mL of acetonitrile solution of PDAA (37.0 mg, 0.30 mmol), copper(I) bromide (7.2 mg, 0.05 mmol) and N,N,N',N',N", N"-pentamethyldiethylenetriamine (PMDETA) (4.3 mg, 0.025 mmol) under a constant purge of Ar. The device was kept in the reaction solution under argon atmosphere overnight. After the reaction, the device was removed, sonicated in pure acetonitrile for 1 min, rinsed with copious amount of pure acetonitrile and water, and then dried under a stream of $N_2$. The resulting P(Q4VP-VBAm)-SWCNT devices were kept under Ar or vacuum while not in use.

Preparation of Cu-containing Control Devices.

Cu-containing devices were fabricated in the same manner as described above except without the addition of PDAA. For control purposes, the devices fabricated with P(4VP-VBAz)-SWCNT and P(Q4VP-VBAz)-SWCNT were soaked into a 5 mL of acetonitrile solution containing CuBr (7.2 mg) and PMDETA (4.3 mg) under a constant purge of Ar, and then kept under argon atmosphere overnight. After the reaction, the devices were removed, sonicated in pure acetonitrile for 1 min, rinsed with copious amount of pure acetonitrile and water, and then dried under a stream of $N_2$.

$CO_2$ Detection Measurement.

The fabricated device was inserted into a 2×30 pin edge connector (TE Connectivity AMP Connectors) mounted on a solderless breadboard, and then enclosed with a custom-built PTFE chamber containing a small gas inlet and outlet. The gold electrodes of the device were connected to a PalmSens EmStat potentiostat with a MUX16 multiplexer. Four mass flow controllers (MFCs, Alicat Scientific) were used to deliver a mixture of various concentration of $CO_2$ in a carrier gas ($N_2$ or air) to the device's enclosure with a total flow rate of 500 mL/min. A water bubbler was connected between one of the MFCs and the inlet of device's enclosure to adjust humidity of the test gas (FIG. 17). The potentiostat applied a constant potential of 0.1 V across the electrodes, and the current for each channel of the device was recorded using PSTrace5 software during 200 s of $CO_2$ exposures. The change in current resulting from exposure to $CO_2$ was converted to the negative change in conductance ($\Delta G/G_0$ (%)=$(I-I_0)/I_0 \times 100\%$, where $I_0$ is initial current), which was taken as the device's response.

Each of the following references is incorporated by reference in its entirety.

(1) Lawlor, D. W.; Mitchell, R. A. C. The Effects of Increasing $CO_2$ on Crop Photosynthesis and Productivity: a Review of Field Studies. *Plant Cell Environ.* 1991, 14, 807-818.

(2) Ontario Ministry of Agriculture, Food and Rural Affairs. Carbon Dioxide in Greenhouses. http://www.omafra.gov.on.ca/english/crops/facts/00-077.htm (accessed Jul. 6, 2018).

(3) Puligundla, P.; Jung, J.; Ko, S. Carbon Dioxide Sensors for Intelligent Food Packaging Applications. *Food Control* 2012, 25, 328-333.

(4) Biji, K. B.; Ravishankar, C. N.; Mohan, C. O.; Srinivasa Gopal, T. K. Smart Packaging Systems for Food Applications: a Review. *J. Food Sci. Technol.* 2015, 52, 6125-6135.

(5) Smolander, M.; Hurme, E.; Ahvenainen, R. Leak Indicators for Modified-Atmosphere Packages. *Trends Food Sci. Tech.* 1997, 8, 101-106.

(6) Kader, A. A.; Zagory, D.; Kerbel, E. L. Modified Atmosphere Packaging of Fruits and Vegetables. *Crit. Rev. Food Sci.* 1989, 28, 1-30.

(7) Hyun, J.-E.; Kim, J.-H.; Choi, Y.-S.; Kim, E.-M.; Kim, J.-C.; Lee, S.-Y. Evaluation of Microbial Quality of Dried Foods Stored at Different Relative Humidity and Temperature, and Effect of Packaging Methods. *J. Food Safety* 2018, 38, e12433.

(8) Ayala-Zavala, J. F.; Del-Toro-Sanchez, L.; Alvarez-Parrilla, E.; Gonzalez-Aguilar, G. A. High Relative Humidity In-Package of Fresh-Cut Fruits and Vegetables: Advantage or Disadvantage Considering Microbiological Problems and Antimicrobial Delivering Systems?. *J. Food Sci.* 2008, 73, R41-R47.

(9) Kauffman, D. R.; Star, A. Carbon Nanotube Gas and Vapor Sensors. *Angew. Chem., Int. Ed.* 2008, 47, 6550-6570.

(10) Fennell, J. F.; Liu, S. F.; Azzarelli, J. M.; Weis, J. G.; Rochat, S.; Mirica, K. A.; Ravnsbæk, J. B.; Swager, T. M. Nanowire Chemical/Biological Sensors: Status and a Roadmap for the Future. *Angew. Chem., Int. Ed.* 2016, 55, 1266-1281.

(11) Liu, S. F.; Lin, S.; Swager, T. M. An Organocobalt-Carbon Nanotube Chemiresistive Carbon Monoxide Detector. *ACS Sens.* 2016, 1, 354-357.

(12) Meyyappan, M. Carbon Nanotube-Based Chemical Sensors. *Small* 2016, 12, 2118-2129.

(13) Bilalis, P.; Katsigiannopoulos, D.; Avgeropoulos, A.; Sakellariou, G. Non-Covalent Functionalization of Carbon Nanotubes with Polymers. *RSC Adv.* 2014, 4, 2911-2934.

(14) Fong, D.; Yeung, J.; McNelles, S. A.; Adronov, A. Decoration of Polyfluorene-Wrapped Carbon Nanotubes via Strain-Promoted Azide-Alkyne Cycloaddition. *Macromolecules,* 2018, 51, 755-762.

(15) Fennell, J. F.; Hamaguchi, H.; Yoon, B.; Swager, T. M. Chemiresistor Devices for Chemical Warfare Agent Detection Based on Polymer Wrapped Single-Walled Carbon Nanotubes. *Sensors* 2017, 17, 982.

(16) Zeininger, L.; He, M.; Hobson, S. T.; Swager, T. M. Resistive and Capacitive □-Ray Dosimeters Based On Triggered Depolymerization in Carbon Nanotube Composites. *ACS Sens.* 2018, 3, 976-983.

(17) Fong, D.; Andrews, G. M.; Adronov, A. Functionalization of Polyfluorene-Wrapped Carbon Nanotubes via Copper-Mediated Azide-Alkyne Cycloaddition. *Poly. Chem.* 2018, 9, 2873-2879.

(18) Fong, D.; Andrews, G. M.; McNelles, S. A.; Adronov, A. Decoration of Polyfluorene-Wrapped Carbon Nanotube Thin Films via Strain-Promoted Azide-Alkyne Cycloaddition. *Poly. Chem.* 2018, DOI: 10.1039/C8PY01003J.

(19) He, M.; Swager, T. M. Covalent Functionalization of Carbon Nanomaterials with Iodonium Salts. *Chem. Mater.* 2016, 28, 8542-8549.

(20) Sakellariou, G.; Priftis, D.; Baskaran, D. Surface-Initiated Polymerization from Carbon Nanotubes: Strategies and Perspectives. *Chem. Soc. Rev.* 2013, 42, 677-704.

(21) Schnorr, J. M.; van der Zwaag, D.; Walish, J. J.; Weizmann, Y.; Swager, T. M. Sensory Arrays of Covalently Functionalized Single-Walled Carbon Nanotubes for Explosive Detection. *Adv. Funct. Mater.* 2013, 23, 5285-5291.

(22) Paoletti, C.; He, M.; Salvo, P.; Melai, B.; Calisi, N.; Mannini, M.; Cortigiani, B.; Bellagambi, F. G.; Swager, T. M.; Francesco, F. D.; Pucci, A. Room Temperature Amine Sensors Enabled by Sidewall Functionalization of Single-Walled Carbon Nanotubes. *RSC Adv.* 2018, 8, 5578-5585.

(23) Yoon, B.; Liu, S. F.; Swager, T. M. Surface-Anchored Poly(4-vinylpyridine)—Single-Walled Carbon Nanotube—Metal Composites for Gas Detection. *Chem. Mater.* 2016, 28, 5916-5924.

(24) Zhu, R.; Desroches, M.; Yoon, B.; Swager, T. M. Wireless Oxygen Sensors Enabled by Fe(II)—Polymer Wrapped Carbon Nanotubes. *ACS Sens.* 2017, 2, 1044-1050.

(25) Soylemez, S.; Yoon, B.; Toppare, L.; Swager, T. M. Quaternized Polymer—Single-Walled Carbon Nanotube Scaffolds for a Chemiresistive Glucose Sensor. *ACS Sens.* 2017, 2, 1123-1127.

(26) Quek, J. Y.; Davis, T. P.; Lowe, A. B. Amidine Functionality as a Stimulus-Responsive Building Block. *Chem. Soc. Rev.* 2013, 42, 7326-7334.

(27) Liu, Y.; Jessop, P. G.; Cunningham, M.; Eckert, C. A.; Liotta, C. L. Switchable Surfactants. *Science* 2006, 313, 958-960.

(28) Yan, Q.; Zhou, R.; Fu, C.; Zhang, H.; Yin, Y.; Yuan, J. $CO_2$-Responsive Polymeric Vesicles that Breathe. *Angew. Chem., Int. Ed.* 2011, 50, 4923-4927.

(29) Yan, Q.; Zhao, Y. Polymeric Microtubules that Breathe: $CO_2$-Driven Polymer Controlled-Self-Assembly and Shape Transformation. *Angew. Chem., Int. Ed.* 2013, 52, 9948-9951.

(30) Zhang, Q.; Wang, W.-J.; Lu, Y.; Li, B.-G.; Zhu, S. Reversibly Coagulatable and Redispersible Polystyrene Latex Prepared by Emulsion Polymerization of Styrene Containing Switchable Amidine. *Macromolecules* 2011, 44, 6539-6545.

(31) Zhang, Q.; Yu, G.; Wang, W.-J.; Yuan, H.; Li, B.-G.; Zhu, S. Preparation of $N_2/CO_2$ Triggered Reversibly Coagulatable and Redispersible Latexes by Emulsion Polymerization of Styrene with a Reactive Switchable Surfactant. *Langmuir* 2012, 28, 5940-5946.

(32) Barkakaty, B.; Browning, K. L.; Sumpter, B.; Uhrig, D.; Karpisova, I.; Harman, K. W.; Ivanov, I.; Hensley, D. K.; Messman, J. M.; Kilbey II, S. M.; Lokitz, B. S. Amidine-Functionalized Poly(2-vinyl-4,4-dimethylazlactone) for Selective and Efficient $CO_2$ Fixing. *Macromolecules* 2016, 49, 1523-1531.

(33) Guo, Z.; Feng, Y.; He, S.; Qu, M.; Chen, H.; Liu, H.; Wu, Y.; Wang, Y. $CO_2$-Responsive "Smart" Single-Walled Carbon Nanotubes. *Adv. Mater.* 2013, 25, 584-590.

(34) Ding, Y.; Chen, S.; Xu, H.; Wang, Z.; Zhang, X. Reversible Dispersion of Single-Walled Carbon Nanotubes Based on a $CO_2$-Responsive Dispersant. *Langmuir* 2010, 26, 16667-16671.

(35) Darabi. A.; Jessop, P. G.; Cunningham, M. F. $CO_2$-Responsive Polymeric Materials: Synthesis, Self-Assembly, and Functional Applications. *Chem. Soc. Rev.* 2016, 45, 4391-4436.

(36) Gouget-Laemmel, A. C.; Yang, J.; Lodhi, M. A.; Siriwardena, A.; Aureau, D.; Boukherroub, R.; Chazalviel, J.-N.; Ozanam, F.; Szunerits, S. Functionalization of Azide-Terminated Silicon Surfaces with Glycans Using Click Chemistry: XPS and FTIR Study. *J. Phys. Chem. C.* 2013, 117, 368-375.

(37) Qiu, J.; Zhou, X.; Mo, Q.; Liu, F.; Jiang, L. Electrostatic Assembled of Keggin-Type Polyoxometalates onto Poly (4-vinylpyridine)-Grafted Poly(vinylidene Fluoride) Membranes. *RSC Adv.* 2014, 4, 48931-48937.

(38) Thiessen, A. N.; Purkait, T. K.; Faramus, A.; Veinot, J. G. C. Lewis Acid Protection: A Method Toward Synthesizing Phase Transferable Luminescent Silicon Nanocrystals. *Phys. Status Solidi A* 2018, 215, 1700620.

(39) Ammu, S.; Dua, V.; Agnihotra, S. R.; Surwade, S. P.; Phulgirkar. A.; Patel, S.; Manohar, S. K. Flexible, All-Organic Chemiresistor for Detecting Chemically Aggressive Vapors. *J. Am. Chem. Soc.* 2012, 134, 4553-4556.

(40) Fréchet, J. M. J.; de Meftahi, M. V. Poly(vinyl Pyridine) s: Simple Reactive Polymers with Multiple Applications. *Br. Polym. J.* 1984, 16, 193-198.

(41) Garcia-España, E.; Gaviria, P.; Latorre, J.; Soriano, C.; Verdejo, B. $CO_2$ Fixation by Copper(II) Complexes of a Terpyridinophane Aza Receptor. *J. Am. Chem. Soc.* 2004, 126, 5082-5083.

(42) Krzywinski, M.; Altman, N. Significance, P Values and t-Tests. *Nat. Methods.* 2013, 10, 1041-1042.

Other embodiments are within the scope of the following claims.

What is claimed is:

1. A composition comprising:
   a polymer including a pyridyl amino side chain and an alkylazide side chain;
   a conductive material associated with the polymer.

2. The composition of claim 1, wherein the conductive material includes a carbon nanotube, a conductive polymer, an inorganic semiconductor, a metal oxide, a carbon fiber, a carbon particle, graphite, graphene, carbon paste, metal particles, conducting ink, or combinations thereof.

3. The composition of claim 1, wherein the polymer is a copolymer of an amine-containing monomer and an alkylazide monomer.

4. The composition of claim 1 wherein the polymer is a copolymer of vinyl pyridine and alkylazido vinyl benzene.

5. A sensor for detecting carbon dioxide comprising:
   a substrate; and
   a composition of claim 1 on the substrate.

6. The sensor of claim 5, wherein the amidine-functional polymer is immobilized on a surface of the substrate.

7. The sensor of claim 5, wherein the carbon conductive material includes a carbon nanotube.

8. The sensor of claim 5, wherein the amidine-functional polymer is a random copolymer.

9. The sensor of claim 5, wherein the amidine-functional polymer is a copolymer of an amine-containing monomer and an amidine-functional monomer.

10. The sensor of claim 9, wherein the amine-containing monomer is a vinyl pyridine.

11. The sensor of claim 10, wherein the vinyl pyridine is quaternized.

12. A method of detecting carbon dioxide comprising:
    exposing a composition of claim 1 to a sample; and
    measuring the conductivity change of the composition.

13. The method of claim 12, wherein the amidine-functional polymer is immobilized on a surface of a substrate.

14. A method of preparing a sensor for detecting an analyte comprising:
    linking a composition of claim 1 to a substrate;
    quaternizing the amino side chain; and
    functionalizing the alkylazide side chain.

15. The method of claim 14, wherein functionalizing the alkylazide side chain includes introducing an amidine-functional group to the side chain.

16. A composition comprising a polymer including amino side chain and an alkylazide side chain, and a conductive material associated with the polymer wherein the polymer is a copolymer of an amine-containing monomer and an alkylazide monomer and wherein the amine-containing monomer is a vinyl pyridine.

17. A composition comprising a polymer including amino side chain and an alkylazide side chain, and a conductive material associated with the polymer wherein the polymer is a copolymer of an amine-containing monomer and an alkylazide monomer and wherein the alkylazide monomer is an alkylazido vinyl benzene.

* * * * *